United States Patent
Murakami et al.

[11] 3,939,150
[45] Feb. 17, 1976

[54] PENICILLIN DERIVATIVES

[75] Inventors: Masuo Murakami, Tokyo; Ichiro Isaka, Hoya; Khozi Nakano, Shiraoka; Isao Souzu, Urawa; Akio Koda, Hoya; Teruaki Ozasa, Urawa; Teruya Kashiwagi, Ageo; Yukiyasu Murakami, Urawa, all of Japan

[73] Assignee: Yamanouchi Pharmaceutical Co., Ltd., Tokyo, Japan

[22] Filed: Oct. 15, 1974

[21] Appl. No.: 514,363

[30] Foreign Application Priority Data
Oct. 19, 1973    Japan............... 48-118390
Nov. 16, 1973    Japan............... 48-129067
Apr. 4, 1974     Japan............... 49-38146
July 27, 1974    Japan............... 49-86355
Sept. 6, 1974    Japan............... 49-102685

[52] U.S. Cl............................. 260/239.1; 424/271
[51] Int. Cl.². .................................. C07D 499/68
[58] Field of Search.............................. 260/239.1

[56] References Cited
UNITED STATES PATENTS
3,268,513   8/1966   Grant et al.................. 260/239.1
3,433,784   3/1969   Long et al................... 260/239.1
3,479,339   11/1969  Holdrege et al............. 260/239.1

Primary Examiner—Gerald A. Schwartz
Attorney, Agent, or Firm—Burgess, Ryan and Wayne

[57] ABSTRACT

The penicillin derivatives represented by the formula

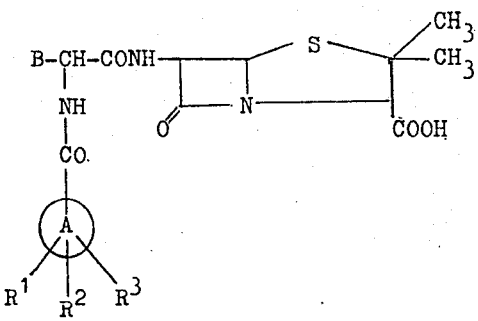

wherein ring A represents a 5- or 6-membered single or fused ring which may contain one or more nitrogen atoms, an oxygen atom, or a sulfur atom; $R^1$, $R^2$, and $R^3$, which may be the same or different, each represents a hydrogen atom, a hydroxy group, a lower alkyl group, a nitro group, a halogen atom, or an oxo group; and B represents a p-hydroxyphenyl group or a 1,4-cyclohexadien-1-yl group, and their nontoxic pharmaceutically acceptable salts.

The compounds are antibiotics having excellent antibacterial activity in particular with respect to the Pseudomonas genus.

1 Claim, No Drawings

PENICILLIN DERIVATIVES

DETAILED DESCRIPTION OF THE INVENTION

The present invention relates to novel penicillin derivatives and more particularly, the invention relates to the acylated derivatives on the amino group of α-amino-p-hydroxybenzylpenicillin (general name: amoxicillin) shown by the formula

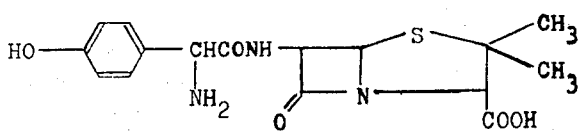

and 6-[D-2-amino-2-(1,4-cyclohexadien-1-yl)acetamido]penicillanic acid (general name: epcillin) shown by the formula

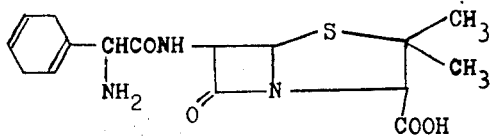

Furthermore, the invention relates, more specifically, to the penicillin derivatives shown by formula III

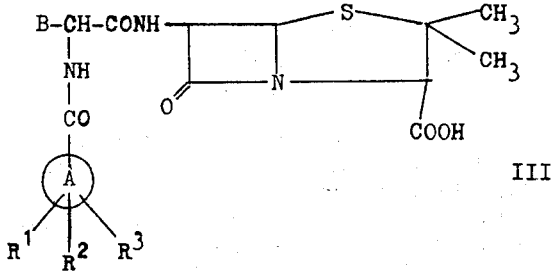

III wherein ring A represents a 5- or 6-membered single or fused ring which may contain one or more nitrogen atoms, an oxygen atom, or a sulfur atom; $R^1$, $R^2$, and $R^3$, which may be the same or different, each represents a hydrogen atom, a hydroxy group, a lower alkyl group, a nitro group, a halogen atom, or an oxo group; and B represents a p-hydroxyphenyl group or a 1,4-cyclohexadien-1-yl group and their nontoxic pharmaceutically acceptable salts.

As the compounds of this invention have excellent antibacterial activity, particularly with respect to the Pseudomonas genus, they are used as antibiotics for the prophylaxis and treatment of diseases of animals including man.

In the compounds of this invention, ring A is a 5- or 6-membered single or fused ring which may contain one or more nitrogen atoms, an oxygen atom, or a sulfur atom and specific examples of the ring are pyrrole, thiophene, furan, 2H-pyrrole, imidazole, pyrazole, pyrrolidine, isothiazole, thiazole, oxazole, isoxazole, imidazolidine, 1,3,4-thiadiazole, tetrazole, cyclopentane, 2H-pyran, 4H-pyran, 2H-thiopyran, 4H-thiopyran, pyridine, pyrazine, pyrimidine, pyridazine, piperidine, piperazine, morpholine, 1,4-dihydropyridine, benzene, 1,4-cyclohexadiene, cyclohexane, benzofuran, chromene, chroman, benzothiophene, naphthothiophene, indole, quinoline, 1,4-dihydroquinoline, isoquinoline, phthalazine, quinoxaline, quinazoline, cinnoline, naphthyridine, naphthalene, etc.

Also, groups $R^1$, $R^2$, and $R^3$, which may be the same or different and are suitably a hydrogen atom; a hydroxyl group; a lower alkyl group such as a methyl group, an ethyl group, a propyl group, an isopropyl group, and a butyl group; a nitro group, a halogen atom, or an oxo group.

In the group of the preferable homologs of the compounds of this invention, ring A is a 5- or 6-membered sisngle or fused ring which may contain one or more nitrogen atoms, an oxygen atom, or sulfur atom; $R^1$ is a hydroxy group or an oxo group; $R^2$ and $R^3$ are hydrogen atoms; and B is a p-hydroxyphenyl group or a 1,4-cyclohexadien-1-yl group. That is, they are the pencillin derivatives represented by the formula

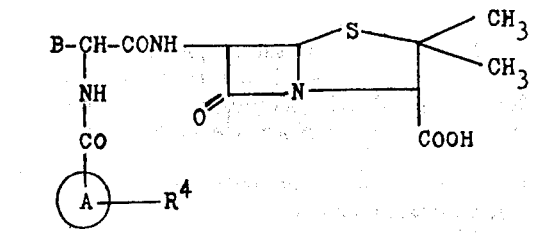

wherein ring A and B have the same significance as described above and $R^4$ represents a hydroxyl group or an oxo group, and their nontoxic pharmaceutically acceptable salts.

In the group of the more preferable compounds of this invention, ring A is a 5- or 6-membered single heterocyclic ring containing one or more nitrogen atom, oxygen atom or sulfur atom, or a fused ring formed by said single heterocyclic ring and a benzene ring; $R^1$ is a hydroxy group or an oxo group; $R^2$ and $R^3$ are hydrogen atoms; and B is a p-hydroxyphenyl group or a 1,4-cyclohexandien-1-yl group. That is, they are the penicillin derivativess represented by the formula

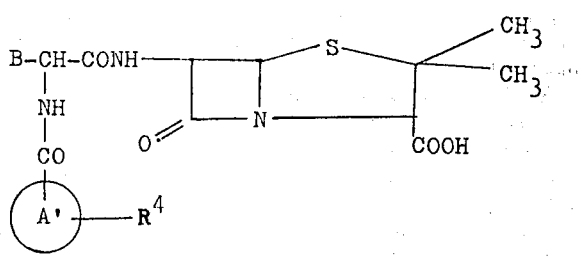

wherein B and R⁴ have the same significance as described above and ring A' represents a 5- or 6-membered single heterocyclic ring containing one or more nitrogen atoms, an oxygen atom, or a sulfur atom or a fused ring formed by said single heterocyclic ring and a benzene ring and their nontoxic pharmaceutically acceptable salts.

Moreover, in the group of preferable compounds of this invention, ring A is a 6-membered single heterocyclic ring containing a nitrogen atom or a sulfur atom; $R^1$ is a hydroxy group or an oxo group; $R^2$ and $R^3$ are hydrogen atoms; and B is a p-hydroxyphenyl group or a 1,4-cyclohexadien-1-yl group. That is, they are the penicillin derivatives represented by the formula

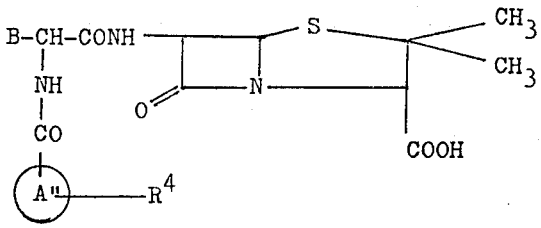

wherein B and R⁴ have the same significance as described above and ring A″ is a 6-membered single heterocyclic ring containing a nitrogen atom or a sulfur atom and their nontoxic pharmaceuticlly acceptable salts.

The most preferable compounds of this invention among the aforesaid compounds, ring A is a 4H-thiopyran ring, $R^1$ is a 4-oxo group, $R^2$ and $R^3$ are hydrogen atoms, and B is a p-hydroxyphenyl group of a 1,4-cyclohexadien-1-yl group. Typical examples of these compounds are α-(4-oxo-4H-thiopyran-3-carboxamido)-p-hydroxybenzylpenicillin and 6-[D-2-(4-oxo-4H-thiopyran-3-carboxamido)-2-(1,4-cyclohexadien-1-yl)acetamido]penicillanic acid.

As the nontoxic pharmaceutically acceptable salts of the compounds of this invention, there are nontoxic metallic salts such as sodium, potassium, calcium, aluminum and magnesium, the ammonium salt and substituted ammonium salts, e.g. salts of such nontoxic amines as trialkylamines, including triethylamine, procaine, dibenzylamine, N-benzyl-β-phenethylamine, l-ephenamine, N-ethylpiperidine, N,N′-bis(dehydroabiethyl)ethylenediamine, N,N′-dibenzylethylenediamine and other amines which have been used to form salts with benzylpenicillin including basic amino acid salts such as arginine and lysine.

Various semi-synthetic penicillins have hitherto been known and among them ampicillin is the most popular and widely sold commercially. However, this antibiotic is practically inactive against the Pseudomonas genus. It is known that amoxicillin which is a semi-synthetic penicillin gives a high concentration in blood by oral administration and also epicillin has selective antibacterial activity to, in particular, gram negative bacteria. However, these antibiotics scarecely show anti-bacterial activity against the Pseudomonas genus.

Now, it is known that when patients with serious disease, as the aged and children, the treatment of the diseases becomes quite difficult, and such patients die frequently. Thus, the discovery of medicaments effective for the treatment of the diseases infected with the Pseudomonas genus has been urgently needed.

In addition, it is known that α-carboxybenzylpenicillin (generic name: carbenicillin) shows activity against the Pseudomonas genus by parenteral administration but its effect is insufficient and it shows weak antibacterial activity against the Klebsiella genus.

Also, as a semi-synthetic penicillin having an activity against Pseudomonas genus, there are known α-(3-guanyl-1-ureido)benzyl-penicillins having the formula

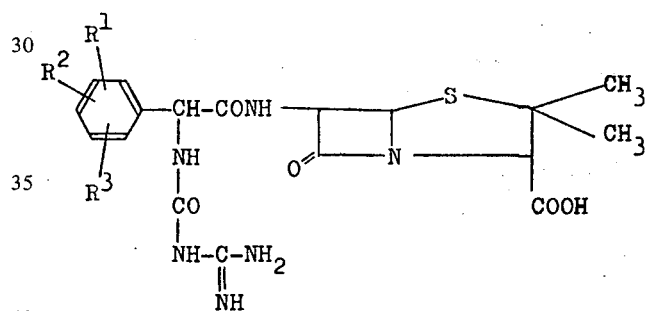

wherein $R^1$, $R^2$, and $R^3$ each represents a hydrogen atom, a nitro group, an alkylamino group, a dialkylamino group, an alkanoylamino group, an amino group, a hydroxy group, an alkanoylcoxy group, an alkyl group, an alkoxy group, a sulfamyl grou, a chlorine atom, an iodine atom, a bromine atom, a fluorine atom, or a trifluoromethyl group (see, U.S. Pat. No. 3,579,501). However, as these compounds have a strong-basic guanylureido group in the structure, they are scarcely soluble in water at the physiological pH and even if they are solubilized in water, the pH is 9.8–9.9 (250 mg/ml), which makes the practical use of these compounds difficult (see, "Antimicrobial agents and Chemotherapy", 12–16(1970) and U.S. Pat. No. 3,711,471).

Now, as the result of various investigations, the inventors have discovered that the acylated derivatives at the amino group of amoxicillin and epicillin have, unexpectedly, low toxicities, excellent antibacterial activities against gram positive bacteria and, more effectively, against gram negative bacteria, and, in particular, excellent antibacterial activities against the Pseudomonas genus and hence these derivatives are useful as antibiotics for the prophylaxis and treatment of diseases of man and animal and are particularly useful for the prophylaxis and treatment of diseases caused by infection with the Pseudomonas genus.

In addition, the acylated derivatives at the amino group of ampicillin as shown by the formula

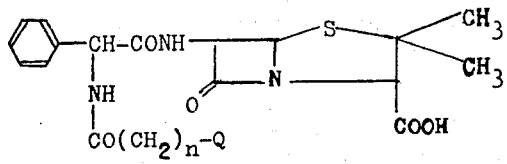

wherein Q represents a heterocyclic ring which may have substituents and $n$ is 0 or 1, are known as semisynthetic penicillins having chemical structures similar to those of the compounds of this invention (see, U.S. Pat. No. 3,433,784). However, in the specification of the U.S. patent, it is disclosed that these penicillins show antibacterial activity against gram positive and gram negative bacteria but there is shown no practical value about the activity. Furthermore, in the specification of Japanese Pat. Publication No. 20,986/1969 corresponding to the above U.S. patent, the values of M. I. C. to the two varieties of Pseudomonas genus are shown. However since the most excellent value is at most 125 $\gamma$/ml., they are almost inactive against the Pseudomonas genus.

Now, the result of the pharmacological tests for the excellent antibacterial activity of the compounds of this invention are shown below.

Experiment 1 (Minimum inhibitory concentration)

a. The minimum inhibitory concentrations for various bacteria (standard strains) are shown in Tables I and II.

Table 1

| | Control | | Compounds of this invention (Example No.) | | | | | |
|---|---|---|---|---|---|---|---|---|
| | Amoxicillin | Carbenicillin | 1 | 2 | 3 | 5 | 6 | 9 |
| Proteus vulgaris OXK US | 0.39 | 1.56 | 0.19 | 0.19 | 0.19 | 0.19 | 0.39 | 0.09 |
| Proteus vulgaris OX 19 US | 6.25 | 0.78 | 3.13 | 0.78 | 0.19 | 1.56 | 0.78 | 0.19 |
| Proteus mirabilis IFMOM-9 | 0.39 | 0.78 | 0.19 | 0.19 | 0.19 | 0.78 | 1.56 | 0.09 |
| Pseudomonas aeruginosa ATCC 8689 | >100 | 100 | 6.25 | 3.13 | 3.13 | 6.25 | 12.5 | 3.13 |
| " 99 (GM-Resistance) | >100 | 50 | 12.5 | 3.13 | 6.25 | 6.25 | 12.5 | 3.13 |
| Pseudomonas ovalis IAM 1002 | 25 | >100 | 6.25 | 6.25 | 6.25 | 3.13 | 6.25 | 1.56 |
| Klebsiella pneumoniae ATCC 10031 | 50 | >100 | 100 | 100 | 25 | 6.25 | 3.13 | 50 |
| Bacillus megatherium 10778 | 0.09 | 3.13 | ≧0.78 | 0.78 | 0.19 | 0.19 | ≧0.19 | ≧0.19 |
| Bacillus subtilis ATCC 6633 | 0.09 | 0.78 | 0.19 | 0.39 | 0.19 | ≧0.19 | ≧0.19 | 0.19 |
| Micrococcus flavus ATCC 10240 | ≧0.09 | 3.13 | 1.56 | ≧0.78 | ≧0.39 | 1.56 | 1.56 | ≧0.78 |
| Staphylococcus aureus FDA 209 P | 0.09 | 0.78 | 0.78 | ≧0.39 | ≧0.19 | 0.39 | 0.78 | ≧0.39 |
| " (shimanishi) | ≧0.39 | 1.56 | ≧3.13 | ≧0.78 | ≧0.78 | 1.56 | ≧1.56 | 1.56 |
| " (onuma) | 3.13 | 12.5 | 25 | ≧12.5 | ≧6.25 | ≧12.5 | 12.5 | 1.25 |

(medium: By heart infusion agar (ph 7.4) plate method)

Table II

| | Control | | Compounds of this invention (Example No.) | | | | | |
|---|---|---|---|---|---|---|---|---|
| | Epicillin | Carbenicillin | 11 | 12 | 13 | 14 | 16 | 19 |
| Proteus vulgaris OX 19 US | 6.25 | 1.56 | 1.56 | 3.13 | 1.56 | 1.56 | 0.78 | 3.13 |
| Pseudomonas aeruginosa ATCC 8689 | 100 | 100 | 6.25 | 6.25 | 12.5 | 12.5 | 12.5 | 50 |
| " 99 (GM-Resistance) | 100 | 50 | 6.25 | 6.25 | 12.5 | 12.5 | 12.5 | 50 |
| Pseudomonas ovalis IAM 1002 | 50 | >100 | 12.5 | 25 | 12.5 | 6.25 | 6.25 | 25 |
| Klebsiella pneumoniae ATCC 10031 | 50 | >100 | 50 | ≧100 | 12.5 | 3.13 | 100 | 6.25 |
| Bacillus megatherium 10778 | ≧0.09 | 3.13 | 0.39 | ≧0.39 | 0.39 | ≧0.19 | 0.39 | ≧0.78 |
| Bacillus subtilis ATCC 6633 | 0.09 | 0.78 | 0.19 | ≧0.39 | 0.19 | ≧0.19 | 0.39 | 1.56 |

Table II-continued

|  | Control | | Compounds of this invention (Example No.) | | | | | |
| --- | --- | --- | --- | --- | --- | --- | --- | --- |
|  | Epicillin | Carbenicillin | 11 | 12 | 13 | 14 | 16 | 19 |
|  | | | M I C ($\mu$/ml) | | | | | |
| *Micrococcus flavus* ATCC 10240 | ≥0.09 | 3.13 | ≥1.56 | ≥1.56 | ≥0.78 | 1.56 | ≥1.56 | 6.25 |
| *Staphylococcus aureus* FDA 209 P | 0.09 | 0.78 | ≥0.19 | ≥0.78 | ≥0.09 | ≥0.09 | ≥0.39 | ≥0.78 |
| " (shimanishi) | ≥0.09 | 1.56 | ≥0.78 | ≥1.56 | ≥0.39 | ≥0.39 | ≥0.78 | 3.13 |
| " (onuma) | ≥3.13 | 12.5 | ≥12.5 | ≥25 | ≥12.5 | ≥6.25 | 12.5 | 25 |

It is clear from the above tables, as regards to the antibacterial activities against the standard strains, the compounds of this invention show excellent antibacterial activities against gram positive bacteria and, in particular, against gram negative bacteria, and especially against Pseudomonas aeruginosa and the compounds of this invention are more active than amoxicillin, epicillin, and carbenicillin.

Table III

| (*Pseudomonas aeruginosa* 35 strain) | | | | | | | |
| --- | --- | --- | --- | --- | --- | --- | --- |
| | | | M I C ($\mu$/ml) | | | | |
| | 1.56 | 3.13 | 6.25 | 12.5 | 25 | 50 | 100 | >100 |
| Carbenicillin | 0 | 0 | 0 | 0 | 3 | 4 | 8 | 20 |
| Present comp. (Example 3) | 2 | 5 | 6 | 6 | 2 | 5 | 2 | 7 |

Table IV

| (*Escherichia coli* 31 strain) | | | | | | | |
| --- | --- | --- | --- | --- | --- | --- | --- |
| | | | M I C ($\mu$/ml) | | | | |
| | 1.56 | 3.13 | 6.25 | 12.5 | 25 | 50 | 100 | >100 |
| Carbenicillin | 1 | 7 | 8 | 6 | 0 | 0 | 0 | 9 |
| Present comp. (Example 3) | 2 | 1 | 8 | 9 | 2 | 0 | 0 | 9 |

Table V

| (*Klebsiella* 78 strain) | | | | | | | | |
| --- | --- | --- | --- | --- | --- | --- | --- | --- |
| | | | M I C ($\mu$/ml) | | | | | |
| | 1.56 | 3.13 | 6.25 | 12.5 | 25 | 50 | 100 | 100 | 400 | >400 |
| Carbenicillin | 1 | 1 | 1 | 0 | 0 | 8 | 8 | 16 | 16 | 27 |
| Present comp. (Example 3) | 0 | 0 | 2 | 17 | 30 | 1 | 1 | 7 | 4 | 16 |

Table VI

| | (One adminstration) Test antibiotics | | |
| --- | --- | --- | --- |
| | Control | | Present compound (Example 3) |
| Amount of administration (mg) | no antibiotics | Carbenicillin | |
| 0 | 0/5 | — | — |
| 15 | — | 1/5 | 2/5 |
| 30 | — | 2/5 | 3/5 |
| 60 | — | 4/5 | 5/5 |

It is clear from the results shown in the above tables, as regards the antibacterial activities against clinical isolated strains, the compounds of this invention show quite high activity against not only *Pseudomonas aeruginosa* but also against Klebsiella as compared with carbenicillin Experiment II (protective effect against experimentally infected mice)

a. Mice (one group included five mice) were infected with pseudomonas aeruginosa NC-5 strain the intraperitoneal route and a solution prepared by dissolving the test antibiotics in sterilized distilled water was once administered by subcutaneous injection immediately after challenge of the test organism and then the numbers of living mice were inspected. The results are shown in Table VI, in which the numerator of the figures show the number of living mice and the denominator shows the number of mice inspected. (The figures shown in Tables VII–IX have the same meaning).

b. Mice (one group included five mice) were infected with pseudomonas aeruginosa NC-5 strain via intraperitoneal route and a solution prepared by dissolving the test substance in sterilized distilled water was administered by subcutaneous injection three times, i. e., immediately after challenge of the test organism, after 2 hours, and after 4 hours. Then, the number of living mice was inspected, the results of which are shown in Table VII.

Table VI

| | (three times administration) Test antibiotics | | |
| --- | --- | --- | --- |
| | Control | | |
| Amount of administration (mg) | no antibiotics | Carbenicillin | Present compound (Example 3) |
| 0 | 0/5 | — | — |
| 2.5 × 3 | — | 2/5 | 5/5 |
| 5 × 3 | — | 0/5 | 5/5 |
| 10 × 3 | — | 5/5 | 5/5 | c. Mice (one group included five mice) were infected with *Pseudomonas aeruginosa* NC-5 strain via the intraperitoneal route and the test substance was orally administered twice, i. e., immediately after challenge of the test organism and after 2 hours. Then, the number of living mice was inspected, the results of which are shown in Table VIII.

Table VIII

| Amount of administration (mg) | Test antibiotics | | |
|---|---|---|---|
| | Control | | Present compound (Example 3) |
| | no antibiotics | amoxicillin | |
| 0 | 0/10 | — | — |
| 25 × 2 | — | 0/5 | 2/5 |
| 50 × 2 | — | 0/5 | 3/5 |
| 100 × 2 | — | 0/5 | 5/5 | d. Mice (one group included five mice) were infected with *Proteus mirabilis* 1287 strain via the intraperitoneal route and a solution prepared by dissolving the test antiobiotics in sterilized distilled water was once administered by subcutaneous injection 2 hours after of challenge of the test organism. Then, the number of living mice was inspected, the results of which are shown in Table IX.

Table IX

| Amount of administration (mg) | Test antibiotics | | |
|---|---|---|---|
| | Control | | Present compound (Example 3) |
| | no antibiotics | Carbenicillin | |
| 0 | 0/5 | — | — |
| 1.25 | — | 0/5 | 1/5 |
| 2.5 | — | 1/5 | 2/5 |
| 5 | — | 2/5 | 4/5 |
| 10 | — | 4/5 | 3/5 |

It is clear from the results shown in Tables VI, VII, VIII, and IX, that the protective effect of the compounds of this invention against mice infection is remarkable, in particular, against *Pseudomonas aeruginosa*.

Experiment III (Toxicity)

a. The minimum lethal doses (MLD) when the compound of this invention was intravenously and subcutaneously administered to male dd-N mice are shown in Table X.

Table X

| Antibiotics | (Acute toxicity) Administration route | M L D (g/Kg) |
|---|---|---|
| Present comp. (Example 3) | i.v. | 3.5 |
| | s.c. | 7.0 |
| Carbenicillin | i.v. | 7.0 |
| | s.c. | >10.0 |

The values were slightly lower than that of carbecillin and it seems to us that the compounds of this invention are clinically useful for large dose administration.

b. Test antibiotics were administered to male Sprague-Dawley rats by subcutaneous injection daily for 7 days. After seven days, animals were sacrificed and estimated for organ weight and serum urea-nitrogen including visual studies of kidney. The results are shown in Table XI.

Table XI (Nephrotoxicity after 1 week subcutaneous injection of 1000 mg/Kg per day into rats.)
Body weights, urine volumes were examined once two days during an experimental period. Tissue weights and serum urea nitrogen of animals sacrificed were measured.

| Antibiotics | Treatments | n | Kidney weights (g) | Serum urea-N (mg/dl) |
|---|---|---|---|---|
| Present compound (Example 3) | 1000mg/Kg/day sc 7 days | 6 | 2.30 ±0.07 | 20.3 ±0.74 |
| Carbenicillin | 1000mg/Kg/day sc 7 days | 4 | 2.53 ±0.07 | 24.0 ±0.90 |
| Kanamycin | 500mg/kg/day sc 7 days | 4 | 3.52 ±0.40 | 70.7 ±23.4 |
| Saline | 5ml/Kg/day sc 7 days | 6 | 2.48 ±0.09 | 21.7 ±0.54 |

The Kanamycin group showed renal hypertropy, ischemia of renal cortex, and abnormal increase of serum urea-nitrogen values. These findings indicated severe renal impairement in the Kanamycin group. On the other hand, there were no abnormal findings in the compounds of this invention and the Carbenicillin group.

c. Glycerol (50%, 4 ml/kg), furocemide (50 mg/kg) and test actibiotics were injected subcutaneously in male Sprague-Dawley rats. It is known that small dose of glycerol given subcutaneously produces mild and reversible renal impairment. Animals of each group were sacrificed 48 hours later to estimate serum ureanitrogen values. The results are shown in Table XII.

Table XII (Acute nephrotoxicity in combination with glycerol and furocemide in rats.) glycerol : 4 ml/Kg s.c. of 50%, furocemide : 50 mg/Kg s.c.

Sprague-Dawley rats male

| Antibiotics | Dose (mg/Kg s.c.) | n | Serum urea nitrogen (mg/dl) |
|---|---|---|---|
| Present compound (Example 3) | 1000 | 4 | 23.3±2.5 |
| Carbenicillin | 1000 | 4 | 29.7±7.2 |
| Cephaloridine | 500 | 4 | 50.7±13.6 |
| CONTROL | — | 5 | 23.5±1.9 |

The results set forth in the table show that there was no remarkable difference between the groups of the compounds of this invention and carbenicillin and the control group but the remarkable increase of serum urea nitrogen was observed relative to the Cephaloridine group. That is, no nephrotoxicity resulted when the test antibiotics of this invention were injected as in the case of injecting carbenicillin.

From the experimental results indicated above, it will be clearly understood that as the compounds of this invention have excellent antibacterial activity against gram positive bacteria and, in particular, gram negative bacterial and further excellent antibacterial activities, in particular, against the Pseudomonas genus among these bacteria, show weak toxicity, and produce no nephrotoxicity; they are useful as antibiotics for the prophylaxis and treatment of diseases of man and animal and are particularly useful for the prophylaxis and treatment of the diseases infected with the Pseudomonas genus.

Now, the compounds of this invention shown by formula III can be prepared by reacting the penicillin shown by formula I

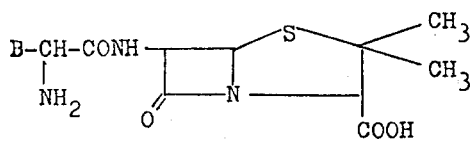

wherein B has the same significance as in formula III with the carboxylic acid shown by formula II

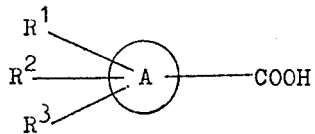

wherein ring A, $R^1$, $R^2$, and $R^3$ have the same signficance as in formula III,
or a reactive derivative thereof.

Furthermore, the compounds of this invention shown by formula III can be also prepared by reacting a benzylpenicillin shown by formula IV

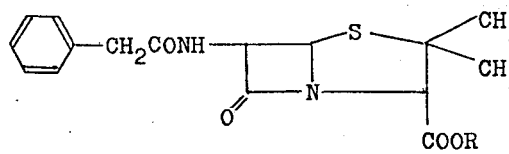

wherein R represents a hydrogen atom, an alkali metal, or an organic ester residue which can be removed under mild conditions, or an ester thereof with a phosphorus halide in an inert solvent to form an iminohalide compound, reacting the product and a lower alcohol to form an iminoether product, reacting the compound with the 2-acylamino-2-substituted acetic acid shown by formula V

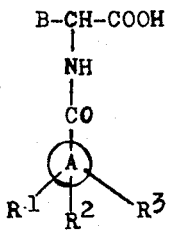

wherein ring A, B, $R^1$, $R^2$, and $R^3$ have the same significance as in formula III, or a reactive derivative thereof, and, if group R is an organic ester residue which can be removed under a mild condition, removing the group.

Still further, the compounds of this invention shown by formula III can be prepared by reacting the 6-aminopenicillanic acid shown by formula VI

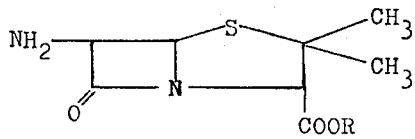

wherein R has the same significance as in formula IV, or an ester thereof with the 2-acylamino-2-substituted acetic acid shown by formula V described above or a reactive derivative thereof and then, if group R is an organic ester residue which can be removed under a mild condition, removing the group.

As the reactive derivatives of the carboxylic acids shown by formula II and the 2-acylamino-2-substituted acetic acids shown by formula V, there are an acid halide such as acid chloride, acid bromide, etc.; an acid azide; an acid anhydride; a mixed acid anhydride prepared by the reaction of an acid shown by formula II or V and an acid or reaction derivative of an acid, for example, alkylhalocarbonate such as ethylchlorocarbonate, ethylbromocarbonate, alkylphosphoric aicd, sulfuric acid, alkylphosphorus acid; an active ester prepared by the reaction of an acid shown by formula II or V and p-nitrophenol; and the like.

Examples of group R of the benzylpenicillin shown by formula IV or the ester thereof and the 6-aminopenicillanic acid shown by formula VI or the ester thereof are a hydrogen atom; an alkalimetal such as sodium, potassium; an organic ester residue which can be removed under a mild condition such as a phenacyl group, a benzyl group which may be substituted by a halogen atom or a nitro group, a 3,5-di-tert-butyl-4-hydroxybenzyl group, and a bis(p-methoxyphenyl)-methyl group.

In producing the compounds of this invention shown by formula III from the compounds shown by formula I, the compounds of formula I may be reacted with, preferably an equimolar amount of a slightly excessive amount of a compound of formula II or the reactive derivative thereof. For example, when an alkyl carbonate mixed acid anhydride is used as the reactive derivative of a compound shown by formula II, the reaction is usually carried out in an organic solvent such as acetone, tetrahydrofuran, dioxane, dimethylformamide, chloroform, dichloromethane, hexamethylphosphoramide, etc., or a mixture thereof, in the presence of a base such as triethylamine, N,N-dimethylaniline, etc., under cooling or at room temeperature. Also, when an acid halide is used as the reactive derivative of a compound shown by formula II, the reaction is usually carried out in an organic solvent such as acetone, tetrahydrofuran, dioxane, dimethylformamide, chloroform, dichloromethane, hexamethylphosphoramide, etc., in the presence of a base such as triethylamine, N,N-dimethylaniline, etc., under cooling or at room temperature or carried out in water in the presence of an alkali suc as sodium hydroxide, potassium hydroxide, etc., under cooling or at room temperature. Furthermore, when an acid azide is used as the reactive derivative of a compound shown by formula II, the reaction is usually carried out in water in the presence of an alkali such as sodium hydroxide, potassium hydroxide, etc., under cooling or at room temperature.

The compounds of this invention thus prepared can be isolated and purified by an ordinary chemical operation such as extraction, recrystallization, etc.

The production of the compounds of this invention shown by formula III from a compound of formula IV is conducted as follows: That is, a compound of formula IV is reacted with a phosphorus halide such as phosphorus pentachloride, phosphorus pentabromide, phosphorus oxychloride, etc., in an inert solvent such as toluene, chloroform, dichloromethane, dichloroethane, trichloroethylene, etc., in the presence of a tertiary amine such as pyridine, N,N-dimethylaniline, triethylamine, etc. When, for example, phosphorus pentachloride is used, the reaction is carried out under cooling to, preferably, 0°C. to −30°C. The tertiary amine added contributes to prevent the cleavage of the lactam ring as the amine combining with the by-produced hydrohalogenic acid. The amount of the tertiary amine is preferably 3–5 mols per mol of a phosphorus halide such as phosphorus pentachloride.

It is preferable to use the phosphorus halide in a slightly excessive amount to the raw material. Then the iminohalide compound obtained is reacted with a lower alcohol wothout isolating from the reaction mixture to form an iminoether compound. As the lower alcohol, a lower aliphatic alcohol such as methanol, ethanol, n-propanol, etc., is usually used.

It is preferable to use an excessive molar amount of the lower alcohol to the raw material. Also, it is preferable to conduct the reaction at almost the same temperature as that in the reaction of forming the iminohalide. Thereafter, the iminoether compound obtained is reacted with a compound of formula V or a reactive derivative thereof.

The compounds of formula V can be prepared by various methods but can be usually obtained by reacting a 2-amino-2-substituted acetic acid shown by formula

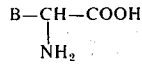

wherein B has the same significance as described above, with a reactive derivative of a compound shown by formula II, such as, for example, the acid chloride or acid anhydride thereof. Also, when group B in the formula of formula V is a p-hydroxybenzyl group, it is unnecessary to protect the hydroxy group at the p-position but the hydroxyl group may be protected by a lower alkanoyl group such as an acetyl group, which can be removed simultaneously with the removal of group R.

The reaction is usually carried out in water or an organic solvent such as an alcohol, acetone, tetrahydrofuran, dimethylformamide, chloroform, dichloromethane, hexamethylphosporamide, etc., in the presence of a base such as triethylamine and dimethylaniline under cooling or at room temperatures.

Then, if group R is an organic ester residue, the group R may be removed under the condition that the lactam bond of lactam ring is not cleaved. The reaction is carried out by treating with an inorganic or organic base such as sodium carbonate, sodium hydrogen-carbonate, sodiumamide, sodium ethoxide, sodium thiophenolate, cyclohexylamine, potassium 2-ethylhexanoate, etc., in water or an organic solvent such as acetone, tetrahydrofuran, dimethylformaide, etc., or a mixture thereof and in this case the compounds of this invention shown by formula III are obtained as the alkali metal salt or amine salt. The product may be converted to the free acid by treating it with an acid in a conventional manner.

In order to produce the compounds of this invention shown by formula III from a compound of formula VI, a compound of formula VI reacted with an equivalent or excessive molar amount of a compound of formula V or the reactive derivative thereof.

The reaction is carried out in a solvent inactive to the reaction, such as, water, an alcohol, acetone, tetrahydrofuran, dimethylformamide, dioxane, chloroform, methylene chloride, hexamethylphosphoramide, etc., or a mixture thereof under cooling or at room temperatures. Then, if group R is an organic ester residue, the group R may be removed under the condition the lactam bond of the lactam ring is not cleaved.

The reaction is carried out by treating with an inorganic or organic base such as sodium carbonate, sodium hydrogencarbonate, sodiumamide, sodium ethoxide, sodium thiophenolate, cyclohexylamine, potassium 2-ethylhexanoate, etc., in water or an organic solvent such as acetone, tetrahydrofuran, dimethylformamide, etc., or a mixture thereof. In this case, a compound of this invention shown by formula III is obtained as an alkali metal salt or an amine salt. The product may be converted into the free acid by treating it with an acid by a conventional procedure.

In addition, a compound of formula V has an asymmetric carbon and in this invention both the optical active substance and the racemic mixture may be used.

As the compounds of this invention are easily soluble in water, the compound can be clinically used as an agent for parenteral administration such as an agent for intravenous injection and an agent for intramuscular injection. For example, when sodium D(-)-6-[α-(p-hydroxyphenyl)-α-(4-oxo-4H-thiopyran-3-yl-carboxanido acetamido]penicillanate is dissolved in water, the pH of the solution is about 5.8 (250 mg/ml).

Now, a compound of this invention, for example, D(-)-6-[p-hydroxyphenyl-α-(4-oxo-4H-thiopyran-3-yl-carboxanido acetamido]penicillanic acid can be obtained as a pure and stable di-hydrate thereof by adding water to the water-containing organic solvent solution thereof. As the di-hydrate is pure and stable, the compound is suitable for formulation. There is no particular limitation about the water-containing organic solvent but a mixture of water and an organic solvent miscible with water, such as acetone, methanol, tetrahydrofuran, ethanol, isopropanol, etc., is usually used. The mixing ratio of the organic solvent and water is not limiting but can be found by checking the point that the compound is dissolved completely in the aforesaid organic solvent by adding gradually water with stirring to the suspension of the compound in the organic solvent. In addition, if the water-containing organic solvent solution keeps up its homogeneity, an organic solvent immiscible with water such as methylene chloride, chloroform, etc., may be added to the solution.

The di-hydrate may be obtained in the form of crystals by adding water to the water-containing organic solvent solution of the a compound of this invention until the solution becomes slightly turbid and, as the case may be, allowing to cool the solution. The di-hydrate may be isolated by a conventional procedure such as filtration and centrifugal separation followed by drying.

Then, the invention will further be described practically by the following examples.

EXAMPLE 1

In 20 ml. of ice water was suspended 420 mg. of amoxicillin tri-hydrate and then the pH thereof was adjusted to 9.2 with 1 N aqueous solution of sodium hydroxide. While stirring the aqueous solution thus formed, 180 mg. of 4,6-dihydroxynicotinic acid azide was added thereto, at 0°–5°C. and then the pH of the solution was maintained at 8–8.5 with 1 N aqueous solution of sodium hydroxide. After stirring the solution further for one hour at the same temperature, the pH of the solution was adjusted to 3 with diluted hydrochloric acid and the precipitates formed were recovered by filtration, washed with water, and dried. The product was dissolved in n-butanol and then a 30% n-butanol solution of sodium 2-ethyl-hexanoate was added to the solution until no further precipitates formed. The precipitates thus formed were recovered by filtration, washed with n-butanol, and dried to provide 300 mg. of α-(4,6-dihydroxynicotimoylamido)-p-hydroxybenzylpenicillin disodium salt having a melting point of higher than 250°C.

Infrared absorption spectra: $\nu KBr_{max} cm^{-1}$: 1765 (β-lactam), 1650 (amide), 1605 (carboxylate).

Nuclear magnetic resonance spectra (D$_6$-DMSO + D$_2$O): δ: 1.48, 1.60 (6H), 4.13 (1H), 6.78 (d), 7.27 (d) (4H), 7.97 (1H).

EXAMPLE 2

In 20 ml. of ice water was suspended 420 mg. of amoxicillin tri-hydrate and then the pH of the suspension was adjusted to 9.2 by adding 1N aqueous solution of sodium hydroxide. While stirring the solution thus obtained, 170 mg. of 4-hydroxynicotinic acid azide was added thereto at 0–5°C. and the mixture was maintained at pH 8–8.5 with 1 N aqueous solution of sodium hydroxide. After further stirring the solution at the same temperature for one hour, the pH of the solution was adjusted to 3 with diluted hydrochloric acid and then 2 g of sodium chloride was added thereto. Then, the precipitates formed were extracted with 10 ml. of a mixture of n-butanol and ethyl acetate of 1 : 2 by volume ratio. The extract was washed with 20% aqueous solution of sodium chloride, dried over anhydrous magnesium sulfate, and then a 30% n-butanol solution of sodium 2-ethylhexanoate was added thereto until no further precipitates formed. The precipitates formed were recovered by filtration, washed with ethyl acetate and dried to provide 300 mg. of α-(4-hydroxynicotinoylamido)-p-hydroxybenzylpenicillin sodium salt having a melting point of 217°–250°C. (decomp.).

Infrared absorption spectra: $\nu KBr_{max} cm^{-1}$: 1770 (β-lactam), 1665 (amide), 1610 (carboxylate).

Nuclear magnetic resonance spectra (D$_2$O): δ: 1.16 (6H), 5.40 (2H), 6.75 (d), 7.25 (d) (4H), 6.55, 7.55, 8.24 (3H).

EXAMPLE 3

In 20 ml. of ice water was suspended 420 mg. of amoxicillin tri-hydrate and then 1 N aqueous solution of sodium hydroxide was added thereto to dissolve the compound. While stirring the solution under cooling to 0°–5°C., 180 mg. of 4-oxo-4H-thiopyran-3-carbonyl chloride and 1 N aqueous solution of sodium hydroxide were slowly added alternately thereto and the mixture was maintained at a pH of 8–8.5. After stirring the solution for one hour at the same temperature, the solution was adjusted to pH 3 with hydrochloric acid and the precipitates formed were recovered by filtration and washed with water.

The solid product was dissolved in 20 ml of a mixture of n-butanol and ethyl acetate of 1 : 2 by volume ratio and the solution was washed with 20 ml. of water and dried over anhydrous magnesium sulfate. Then, a 30% n-butanol solution of sodium 2-ethylhexanoate was added to the solution until no further precipitates formed. The precipitates formed were recovered by filtration, washed with ethyl acetate, and dried to provide 350 mg. of α-(4-oxo-4H-thiopyran-3-carboxamido)-p-hydroxybenzylpenicillin sodium salt having a melting point of 226°–230°C. (decomp.).

Infrared adsorption spectra: $\nu KBr_{max} cm^{-1}$: 1765 (lactam), 1650 (amide), 1595 (carboxylate).

Nuclear magnetic resoance spectra (D$_2$O):

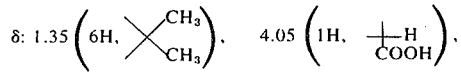

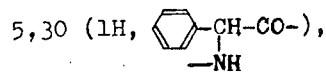

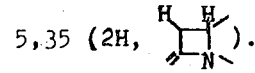

Preparation of the starting material:

In 30 ml. of methylene chloride was dispersed 3.12 g. of 4-oxo-4H-thiopyran-3-carboxylic acid and after adding 1.5 ml. of thionyl chloride and 2 drops of dimethylformamide, the mixture was refluxed with stirring. After about 4 hours, the generation of hydrogen chloride gas ceased.

By concentrating the reaction mixture under a reduced pressure, 3.4 g. of 4-oxo-4H-thiopyran-3-carbonyl chloride was obtained.

Infrared absorption spectra: $\nu CH_2Cl_{2 cm}^{-1}$: 1780 (—COCl), 1730 (>CO).

EXAMPLE 4

A mixture of 420 mg. of amoxicillin tri-hydrate, 300 mg. of anhydrous magnesium sulfate, 0.28 ml. of triethylamine, 10 ml. of dichloromethane, and 2 ml. of hexamethyl-phosphoramide was stirred for 1 hour at room temperature and then magnesium sulfate was filtered off to provide a solution of amoxicillin triethylamine salt. After cooling the solution to temperatures of from −10°C. to −20°C., 160 mg. of salicyloyl acid chloride was added and the mixture was stirred for 2 hours. The reaction mixture formed was concentrated under a reduced pressure at temperatures lower than 20°C., and the residue was dissolved in 20 ml. of water and the pH thereof was adjusted to 3 with diluted hydrochloric acid, whereby precipitates formed. The precipitates were recovered by filtration, washed with water, and then dissolved in ethyl acetate followed by washing with water. The ethyl acetate solution was dried over anhydrous magnesium sulfate, 0.6 ml. of a 30% n-butanol solution of sodium 2-ethylhexanoate was added thereto, and then ether was added until no further precipitate formed. The precipitates formed were recovered by filtration, washed with ether, and dried to provide 200 mg. of α-(2-hydroxy-benzamido)-p-hydroxybenzylpenicillin sodium salt having a melting point of 202°–204°C. (decomp.).

Infrared absorption spectra: $\nu KBr_{max} cm^{-1}$: 1765 (β-lactam), 1635 (amide), 1600 (carboxylate).

Nuclear magnetic resonance spectra (CD$_3$OD): δ: 1.54 (d) (6H), 9.19 (1H), 5.49 (q) (2H), 5.72 (1H), 6.75–8.0 (aromatic 8H).

EXAMPLE 5

A mixture of 420 mg. of amoxicillin tri-hydrate, 300 mg. of anhydrous magnesium sulfate, 0.28 ml. of triethylamine, 10 ml. of dichloromethane, and 2 ml. of hexamethylphosphoramide was stirred for one hour at room temperature and then magnesium sulfate was filtered off to provide a solution of amoxicillin triethylamine salt.

A mixture of 190 mg. of 4-hydroxyquinoline-3-carboxylic acid, 10 ml. of dichloromethane, 2 ml. of hexamethylphosphoramide, and 0.14 ml. of triethylamine was cooled to from −10°C. to −5°C. and a mixture of 0.1 ml. of ethyl chlorocarbonate and 2 ml. of dichloromethane was added thereto dropwise over a period of 10 minutes. After further stirring the mixture for 15 minutes, the reaction mixture was added dropwise to the solution of amoxicillin triethylamine salt prepared above over a period of 10 minutes and the mixture was further stirred for 30 minutes at temperatures of from −10°C. to −5°C. The reaction mixture obtained was concentrated under reduced pressure at temperatures of lower than 20°C. and the residue was dissolved in 20 ml. of water. When the solution thus obtained was adjusted to pH 3 with diluted hydrochloric acid, precipitates formed. The precipitates were recovered by filtration, washed with water, and dissolved in 10 ml. of ethyl acetate. The solution was washed with water and dried over anhydrous magnesium sulfate. Thereafter, a 30% n-butanol solution of sodium 2-ethylhexanoate was added to the solution until no further precipitate formed. The precipitates formed were recovered by filtration, washed with ethyl acetate, and dried to provide 250°mg. of α-(4-hydroxyquinolin-3-carboxamido)-p-hydroxybenzylpenicillin sodium salt having a melting point of 234°–238°C. (decomp.).

Infrared absorption spectra: $\nu KBr_{max} cm^{-1}$: 1770 ($\beta$-lactam), 1660 (amide), 1610 (carboxylate).

Nuclear magnetic resonance spectra (D$_2$O): δ: 1.52 (6H), 4.31 (1H), 5.66 (2H), 5.59 (1H), 6.9–8.4 (aromatic 9H).

EXAMPLE 6

A mixture of 420 mg. of amoxicillin tri-hydrate, 300 mg. of anhydrous magnesium sulfate, 0.28 ml. of triethylamine, 10 ml. of dichloromethane, and 2 ml. of haxamethylphosphoramide was stirred for 1 hour at room temperature and then magnesium sulfate was filtered off to provide a solution of amoxicillin triethylamine salt.

A mixture of 260 mg. of 1-ethyl-6-nitro-4-oxo-1,4-dihydroquinoline-3-carboxylic acid, 10 ml. of dichloromethane, 2 ml. of hexamethylphosphoramide, and 0.14 ml. of triethylamine was cooled to temperatures of from −10°C. to −5°C. and then a mixture of 0.1 ml. of ethyl chlorocarbonate and 2 ml. of dichloromethane was added dropwise to the above mixture over a period of 10 minutes. After further stirring the mixture for 15 minutes, the reaction mixture was added dropwise to the solution of amoxicillin triethylamine salt prepared above over a period of 10 minutes and the mixture was further stirred for 30 minutes at temperatures of from −10°C to −5°C. The reaction mixture was concentrated under reduced pressure at temperatures lower than 20°C and the residue was dissolved in 10 ml. of water. When the solution was adjusted to pH 3 with diluted hydrochloric acid, the resulting precipitates were recovered by filtration and washed with water. The solid obtained was dissolved in 10 ml. of a mixture of n-butanol and ethyl acetate of 1 : 2 by volume ratio and the solution was washed with water and dried over anhydrous magnesium sulfate. Then, a 30% n-butanol solution of sodium 2-ethylhexanoate was added to the solution until no further precipitates formed. The precipitates formed were recovered by filtration, washed with ethyl acetate and dried to provide 250 mg. of α-(1-ethyl-6-nitro-4-oxo-1,4-dihydroquinoline-3-carboxamido)-p-hydroxybenzylpenicillin sodium salt having a melting point of 244°–256°C. (decomp.).

Infrared absorption spectra:
$\nu KBr_{max} cm^{-1}$: 1770 ($\beta$-lactam), 1660 (amide), 1610 (carboxylate).

Nuclear magnetic resonance spectra (D$_2$O): δ: 1.34 (6H), 4.07 (1H), 5.34 (3H), 6.6–8.2 (aromatic 8H).

EXAMPLE 7

A mixture of 420 mg. of amoxicillin tri-hydrate, 300 mg. of anhydrous magnesium sulfate, 0.28 ml. of triethylamine, 10 ml. of dichloromethane, and 2 ml. of hexamethylphosphoramide was stirred for 1 hour at room temperature and magnesium sulfate was filtered off to provide a solution of amoxicillin triethylamine salt.

A mixture of 130 mg. of picolinic acid, 10 ml. of dichloromethane, and 0.14 ml. of triethylamine was cooled to temperatures of from −10°C. to −5°C. and then a mixture of 0.1 ml. of ethyl chlorocarbonate and 2 ml. of dichloromethane was added dropwise to the mixture over a period of 10 minutes. The resultannt mixture was stirred for 15 minutes and added dropwise to the solution of amoxicillin triethylamine salt prepared above while cooling to −10°C over a period of 10 minutes followed by stirring further for 30 minutes at temperatures of from −10°C. to −5°C.

The reaction mixture thus obtained was concentrated under a reduced pressure at temperatures of lower than 20°C. and the residue was dissolved in 20 ml. of water. When the solution thus prepared was adjusted to pH 3, with diluted hydrochloric acid, precipitates formed, which were recovered by filtration and washed with water. The solid obtained was dissolved in 10 ml. of a mixture of n-butanol and ethyl acetate at a volume ratio of 1:2 and the solution was washed with water and dried over anhydrous magnesium sulfate.

Thereafter, a 30% n-butanol solution of sodium 2-ethylhexanoate was added to the solution prepared above until no further precipitates formed. The precipitates formed were recovered by filtration, washed with ethyl acetate and dried to provide 250 mg. of α-(2-pyridylcarboxamido)-p-hydroxybenzylpenicillin sodium salt having a melting point of 211°–215°C. (decomp.).

Infrared absorption spectra: $\nu_{max}^{KBr} cm^{-1}$: 1765 ($\beta$-lactam), 1660 (amide), 1600 (carboxylate).

Nuclear magnetic resonance spectra (CD$_3$OD): δ: 1.58 (6H), 4.23 (1H), 5.54 (2H), 5.83 (1H), 6.88 (d), 7.14 (d) (4H).

EXAMPLE 8

A mixture of 420 mg. of amoxicillin tri-hydrate, 300 mg. of anhydrous magnesium sulfate, 0.28 ml. of triethylamine, 10 ml. of dichloromethane, and 2 ml. of hexamethylphosphoramide amide was stirred for 1 hour at room temperature and then magnesium sulfate was filtered off to provide a solution of amoxicillin triethylamine salt.

A mixture of 130 mg. of 2-thiophenecarboxylic acid, 10 ml. of dichloromethane, and 0.14 ml. of triethylamine was cooled to temperatures of from −10°C. to −5°C. and then a mixture of 0.1 ml. of ethyl chlorocarbonate and 2 ml. of dichloromethane was added dropwise to the mixture over a period of 10 minutes. After stirring the mixture for 15 minutes, the reaction mixture was added dropwise to the solution of amoxicillin triethylamine salt prepared above while cooling to −10°C. over a period of 10 minutes and the mixture was further stirred for 30 minutes at temperatures of from −10°C. to −5°C.

The reaction mixture thus obtained was concentrated under reduced pressure at temperatures lower than 20°C. and the residue was dissolved in 20 ml. of water. The solution thus prepared was adjusted to pH 3 with diluted hydrochloric acid, whereby precipitates formed. The precipitates were recovered by filtration and washed with water. The solid obtained was dissolved in 10 ml. of a mixture of n-butanol and ethyl acetate of 1 : 2 by volume ratio and the solution formed was washed with water and dried over anhydrous magnesium sulfate. Thereafter, a 30% n-butanol solution of sodium 2-ethylhexanoate was added to the aforesaid solution until no further precipitates formed. The precipitates formed were recovered by filtration and then ether was further added to the filtrate until no further precipitates formed. The precipitates formed were also recovered by filtration and combined with the precipitates recovered previously. They were washed with ether and dried to provide 300 mg. of α-(2-thienylcarboxamido)-p-hydroxybenzylpenicillin sodium salt having a melting point of 218°–224°C. (decomp.).

Infrared absorption spectra: $\nu_{max}^{KBr} cm^{-1}$: 1775 (β-lactam), 1665 (amide), 1610 (carboxylate).

EXAMPLE 9

A mixture of 420 mg. of amoxicillin tri-hydrate, 300 mg. of anhydrous magnesium sulfate, 0.28 ml. of triethylamine, 10 ml. of dichloromethane, and 2 ml. of hexamethylphosphoramide was stirred for 1 hour at room temperature and then magnesium sulfate was filtered off to provide a solution of amoxicillin triethylamine salt.

A mixture of 160 mg. of 2,4-dihydroxypyrimidine-5-carboxylic acid, 10 ml. of dichloromethane, 2 ml. of hexamethylphosphoramide, and 0.14 ml. of triethylamine was cooled from −10°C. to −5°C. and a mixture of 0.1 ml. of ethyl chlorocarbonate and 2 ml. of dichloromethane was added dropwise to the above mixture over a period of 10 minutes. After stirring the mixture for 15 minutes, the reaction mixture was added dropwise to the solution of amoxicillin triethylamine salt prepared above while cooling to −10°C. over a period of 10 minutes. The mixture was further stirred for 30 minutes at temperatures of from −10°C. to −5°C.

The reaction mixture was concentrated under reduced pressure at temperatures lower than 20°C. and the residue was dissolved in 20 ml. of water. When the solution was adjusted to pH 3 with diluted hydrochloric acid, precipitates formed, which were recovered by filtration and washed with water. The solid obtained was dissolved in 10 ml. of a mixture of n-butanol and ethyl acetate of 1 : 2 by volume ratio and the solution was washed with water and dried over anhydrous magnesium sulfate. Thereafter, a 30% h-butanol solution of sodium 2-ethylhexanoate was added to the solution until no further precipitate formed. The precipitates formed were recovered by filtration, washed with ethyl acetate, and dried to provide 400 mg. of α-(2,4-dihydroxyprimidine-5-carboxamido)-p-hydroxybenzylpenicillin disodium salt having a melting point higher than 250°C.

Infrared absorption spectra: $\nu_{max}^{KBr} cm^{-1}$: 1770 (β-lactam), 1680 (amide), 1605 (carboxylate).

Nuclear magnetic resonance spectra (CD₃OD + D₆-DMSO) δ: 1.55 (6H), 4.14 (1H), 5.35–5.66 (3H), 6.78, 7.30 (4H), 8.37 (1H).

EXAMPLE 10

A mixture of 420 mg. of amoxicillin tri-hydrate, 300 mg. of anhydrous magnesium sulfate, 0.28 ml. of triethylamine, 10 ml. of dichloromethane, and 2 ml. of hexamethylphosphoramide amide was stirred for 30 minutes at room temperature and then magnesium sulfate was filtered off to provide a solution of amoxicillin triethylamine salt.

A mixture of 0.14 g. of 2-oxo-2H-pyran-5-carboxylic acid, 20 ml. of dichloromethane, and 0.14 ml. of triethylamine was cooled from −10°C to −15°C. and then a mixture of 0.1 ml. of ethyl chlorocarbonate and 2 ml. of dichloromethane was added dropwise to the mixture over a period of 10 minutes. After stirring the mixture further for 45 minutes, the reaction mixture was added dropwise to the solution of amoxicillin triethylamine salt prepared above at temperatures of from −20°C. to −30°C. and the mixture was stirred for 10 minutes at the same temperature.

The reaction mixture was concentrated under reduced pressure at low temperature and the residue was dissolved in 20 ml. of ice water. When the solution was adjusted to pH 2 with diluted hydrochloric acid, precipitates formed, which were recovered by filtration and washed with water. The precipitates were dissolved in 20 ml. of ethyl acetate and after filtering off insoluble materials, the filtrate was dried over anhydrous magnesium sulfate and then a 30% n-butanol solution of sodium 2-ethylhexanoate was added thereto until no further precipitates formed. The precipitates were recovered by filtration, washed with ethyl acetate and ether, and dried to provide 275 mg. of a yellow powder of α-(2-oxo-2H-pyran-5-carboxamido)-p-hydroxybenzylpenicillin sodium salt having a melting point of 214°–220°C. (decomp.):

Infrared resonance spectra: $\nu_{max}^{KBr} cm^{-1}$: 1770 (β-lactam), 1625 (ketone), 1665 (amide), 1610 (carboxylate).

EXAMPLE 11

A mixture of 1 g. of epicillin, 0.5 g. of anhydrous magnesium sulfate, 0.7 ml. of triethylamine, 5 ml. of hexamethylphosphoramide, and 25 ml. of dichloromethane was stirred for 30 minutes at room temperature and then magnesium sulfate was filtered off to provide a dichloromethane solution of epicillin triethylamine salt.

The solution thus obtained was cooled to −20°C. and after adding thereto 0.5 g. of 4-hydroxynicotinoyl chloride and 0.4 ml. of triethylamine, the mixture was stirred for 2 hours at the same temperature. Thereafter, dichloromethane was distilled off under reduced pressure from the reaction mixture. The residue was dissolved in 25 ml. of cold water, 25 ml. of a mixture of n-butanol and ethyl acetate of 1 : 5 by volume ratio was added to the solution in layer and after adjusting to pH 2 with 10% hydrochloric acid and stirring the mixture, a small amount of insoluble materials was filtered off. The organic layer was separated, washed with a 5% aqueous solution of sodium chloride, and dried over anhydrous magnesium sulfate.

Then, a 30% n-butanol solution of sodium 2-ethylhexanoate was added to the organic layer until no further precipitates formed. The precipitates formed were recovered by filtration and reprecipitated from methanol and ether to provide 0.25 g. of a yellow powdery crystal sodium 6-[D-2(4-hydroxynicotinoyl-amino)-2-(1,4-cyclohexadien-1-yl)acetamido]penicillamate having a melting point of 229°–232°C. (decomp.).

Infrared absorption spectra: $\nu_{max}^{KBr}$cm$^{-1}$: 3420, 3250 (OH, NH), 1770 ($\beta$-lactam), 1660 (amide), 1610 (carboxylate):

Nuclear magnetic resonance spectra (D$_2$O):

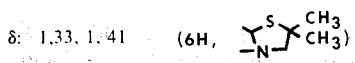
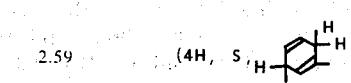
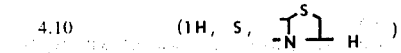
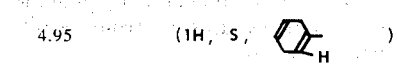
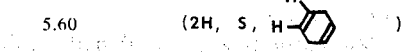
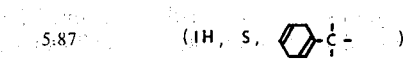
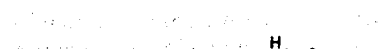

Preparation of the staring material:

In 4000 ml. of dichloromethane was suspended 200 g. of 4-hydroxynicotinic acid and then 250 ml. of triethylamine was added to the suspension at room temperature followed by stirring to dissolve 4-hydroxynicotinic acid. The solution thus obtained was cooled to −10°C. and 132 ml. of thionyl chloride was added dropwise to the solution with stirring. After stirring the mixture for 2 hours at 0°–5°C., the crystals which had formed were recovered by filtration, washed with dichloromethane, and dried over phosphorus pentoxide under reduced pressure to provide 206 g. (yield 91%) of 4-hydroxynicotinoyl chloride.

Melting point 156°–160°C. (decomp.)

Infrared absorption spectra: $\nu_{max}^{KBr}$cm$^{-1}$: 3400 (OH), 1770 ($\supset$C=O).

Elemental analysis for C$_6$H$_4$NO$_2$Cl: Calculated: Cl, 22.50%. Found: Cl, 21.64%

EXAMPLE 12

In 20 ml. of ice water was suspended 1 g. of epicillin and while stirring the suspension, 2.5 ml. of 1 N-sodium hydroxide solution was added thereto to dissolve epicillin. While stirring the solution and cooling to 0°–5°C., 0.5 g. of 4,6-dihydroxynicotinoyl acid chloride was added and then about 2.5 ml. of 1N-sodium hydroxide solution was added slowly dropwise to the mixture and the mixture was maintained at a pH of 8–8.5 for 30 minutes. A small amount of perlite (made by Toko Perlite K. K.) was added to the reaction mixture and then the reaction mixture was filtered. The filtrate was adjusted to pH 2 with 10% hydrochloric acid and the crystals thus formed were recovered by filtration and washed with water. After drying, the crystals were dissolved in 20 ml. of isopropanol and then a small amount of insoluble materials were filtered off. A 30% n-butanol solution of sodium 2-ethylhexanoate was added to the filtrate until no further precipitates formed and after adding an equal amount of acetone and stirring the mixture, the precipitates which formed were recovered by filtration and washed with acetone to provide 0.65 g. of a white powdery crystal of disodium 6-[D-2-(4,6-dihydroxynicotinoylamino)-2-(1,4-cyclohexadiene-1-yl)acetamido]penicillanate having a melting point of 248°–253°C. (decomp.).

Infrared absorption spectra: $\nu_{max}^{KBr}$cm$^{-2}$: 3400, 3270 (OH, NH), 1770 ($\beta$-lactam), 1660 (amide), 1610 (carboxylate).

Nuclear magnetic resonance spectra (D$_2$O):

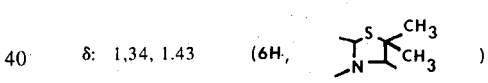
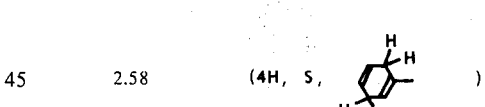
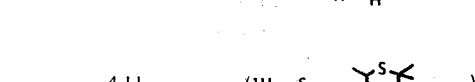
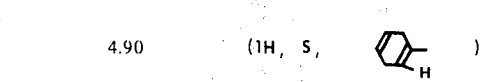
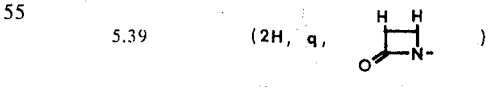
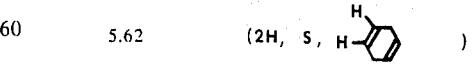
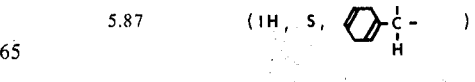
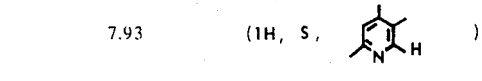

EXAMPLE 13

In 20 ml. of ice water was suspended 1g. of epicillin and while stirring the suspension, 2.5 ml. of 1N-sodium hydroxide solution was added thereto to dissolve epicillin. While stirring the solution under cooling to 0°–5°C., 0.44 g. of 4-thiopyrone-3-carbonyl chloride was added to the solution and then 1N-sodium hydroxide solution was added slowly dropwise to the mixture and the mixture was maintained at a pH of 8–8.5 for 30 minutes. Then, 20 ml. of a mixture of n-butanol and ethyl acetate of 1 : 2 by volume ratio was added to the reaction mixture in layer and while stirring the mixture, the pH was adjusted to 2 with 10% hydrochloric acid. The organic layer was separated, washed with water, and dried over anhydrous magnesium sulfate.

A 30% n-butanol solution of sodium 2-ethylhexanoate was added to the solution until no further precipitate formed and the precipitates were recovered by filtration and washed with ethyl acetate. By re-precipitating the precipitates from methanol and ether, 0.45 g. of light-brown powdery crystals of sodium 6-[D-2-(4-thiopyrone-3-carbonylamino)-2-(1,4-cyclohexadien-1-yl)acetamido]penicillanate having a melting point of 215°–220°C. (decomp.) was obtained.

Infrared absorption spectra: $\nu_{max}^{KBr}$cm$^{-1}$: 3400, 3250 (OH, NH), 1765 ($\beta$-lactam), 1660 (amide), 1600 (carboxylate).

Nuclear magnetic resonance spectra (D$_2$O):

δ: 1.37, 1.43  (6H,  )

2.57  (4H, s,  )

4.17  (1H, s,  )

4.93  (1H, s,  )

5.44  (2H, q,  )

5.60  (2H, s,  )

5.87  (1H, s,  )

7.02  (1H, d,  )

8.02  (1H, q,  )

9.01  (1H, d,  )

EXAMPLE 14

A mixture of 1 g. of epicillin, 0.5 g. of anhydrous magnesium sulfate, 0.7 ml. of triethylamine, 5 ml. of hexamethylphosphoramide, 25 ml. of dichloromethane was stirred for 30 minutes at room temperature and then magnesium sulfate was filtered off to provide a dichloromethane solution of epicillin triethylamine salt.

In 10 ml. of hexamethylphosphoramide was suspended 0.48 g. of 4-quinolone-3-carboxylic acid and then 0.4 ml. of triethylamine was added to the suspension to dissolve the carboxylic acid. Then, 2 ml. of a dichloromethane solution of 0.25 ml. of ethyl chlorocarbonate was added dropwise to the solution at 0°–5°C. and the mixture was stirred for one hour at the same temperature.

To the resulting solution was added dropwise the dichloromethane solution of epicillin triethylamine salt prepared above at temperatures of from −20°C. to −30°C. over a period of 1 hour.

The reaction mixture obtained was concentrated under reduced pressure at low temperature and the residue was dissolved in 50 ml. of cold water. When the solution was adjusted to pH 2 with 10% hydrochloric acid, the precipitates which had formed, which were recovered by filtration and extracted twice each time with 10 ml. of ethyl acetate.

The ethyl acetate extracts were combined, washed with a 5% aqueous solution of sodium chloride, and dried over anhydrous magnesium sulfate. Then, 1.5 ml. of a 30% n-butanol solution of sodium ethylhexanoate was added to the ethyl acetate solution and after adding thereto 50 ml. of ether, the precipitates formed were recovered by filtration. By re-precipitating the precipitates from a mixture of methanol and ether, 0.55 g. of yellowish white powdery crystals of sodium 6-[D-2-(4-quinolone-3-carbonylamino)-2-(1,4-cyclohexadien-1-yl)acetamido]penicillanate was obtained.

Melting point 226°–229°C. (decomp.)

Infrared absorption spectra: $\nu_{max}^{KBr}$cm$^{-1}$: 3400, 3250 (OH, NH), 1765 ($\beta$-lactam), 1660 (amide), 1600 (carboxylate).

Nuclear magnetic resonance spectra (D$_2$O):

δ: 1.37, 1.43  (6H,  )

2.57  (4H, s,  )

4.17  (1H, s,  )

-continued

| | | |
|---|---|---|
| 4.93 | (1H, s, | [phenyl-H]) |
| 5.44 | (2H, q, | [β-lactam CH]) |
| 5.60 | (2H, s, | H-[cyclohexadienyl]-) |
| 5.87 | (1H, s, | [cyclohexadienyl]-CH-) |
| 7.1–7.5 | | (4H, m, aromatic ring) |
| 8.13 | (1H, s, | [pyridine-CONH]) |

EXAMPLE 15

A mixture of 1 g. of epicillin, 0.5 g. of anhydrous magnesium sulfate, 0.7 ml. of triethylamine, 5 ml. of hexamethylphosphoruamide, and 25 ml. of dichloromethane was stirred for 30 minutes at room temperature, magnesium sulfate was filtered off to provide a dichloromethane solution of epicillin triethylamine salt.

A mixture of 0.31 g. of picolinic acid, 0.4 ml. of triethylamine and 30 ml. of dichloromethane was cooled to 0°–5°C. and after adding dropwise thereto a solution of 0.25 ml. of ethyl chlorocarbonate in 2 ml. of dichloromethane at the same temperature, the mixture was stirred for 1 hour. To this solution was added dropwise a dichloromethane solution of epicillin triethylamine salt prepared above at temperatures of from −20°C. to −30°C. and the mixture was then stirred for 1 hour. The reaction mixture was concentrated under reduced pressure at low temperature and the residue was dissolved in 50 ml. of cold water. The solution was adjusted to pH 2 with 10% hydrochloric acid and the precipitates were recovered by filtration and washed with water. The precipitates were dissolved in 50 ml. of a mixture of n-butanol and ethyl acetate of 1:4 by volume ratio and a small amount of insoluble materials was filtered off.

The filtrate was washed with a 5% aqueous solution of sodium chloride and then dried over anhydrous magnesium sulfate. Then, 1.5 ml. of a 30% n-butanol solution of sodium 2-ethylhexanoate was added to the filtrate and after adding thereto 50 ml. of ether, the precipitates which had formed were recovered by filtration.

By re-precipitating the precipitates from a mixture of methanol and ethyl acetate, 0.6 g. of white powdery crystals of sodium 6-[D-2-(pyridine-2-carbonylamino)-2-(1,4-cyclohexadien-1-yl)acetamido]penicillamate was obtained.

Melting point 199°–203°C. (decomp.)

Infrared absorption spectra: $\nu_{max}^{KBr} cm^{-1}$: 3360–3400 (OH, NH), 1765 (β-lactam), 1660 (amide), 1605 (carboxylate).

Nuclear magnetic resonance spectra (CD$_3$OD):

| δ: 1.59, 1.67 | (6H, | [gem-dimethyl]) |
|---|---|---|
| 2.77 | (4H, s, | [cyclohexadiene CH$_2$]) |
| 4.26 | (1H, s, | [penicillin C3-H]) |
| 5.31 | (1H, s, | [cyclohexadienyl-H]) |
| 5.59 | (2H, s, | [β-lactam CH]) |
| 5.67 | (2H, s, | H-[cyclohexadienyl]-) |
| 5.99 | (1H, s, | [cyclohexadienyl]-CH-) |
| 7.57 | (1H, q, | [pyridine-H]-CO-) |
| 8.02 | (1H, q, | [pyridine-H]-CO-) |
| 8.14 | (1H, d, | [pyridine-H]-CO-) |
| 8.67 | (1H, d, | H-[pyridine]-CO-) |

EXAMPLE 16

A mixture of 1 g. of epicillin, 0.5 g. of anhydrous magnesium sulfate, 0.7 ml. of triethylamine, and 5 ml. of hexamethylphosphoramide amide, and 25 ml. of dichloromethane was stirred for 30 minutes at room temperature and then magnesium sulfate was filtered off to provide a dichloromethane solution of epicillin triethylamine salt.

Then, a solution consisting of 0.4 g. of 2,4-dihydroxypyrimidine-5-carboxylic acid, 30 ml. of dichloromethane, 10 ml. of hexamethylphosphoramide, and 0.36 ml. of triethylamine was cooled to temperatures of from −10°C. to −15°C. and then 5 ml. of a dichloromethane solution of 0.24 ml. of ethyl chlorocarbonate was added dropwise to the solution followed by stirring for one hour at the same temperature. To the resulting solution was added dropwise the solution of the dichloromethane solution of epicillin triethylamine salt prepared above at temperatures of from −20°C. to −30°C. and the mixture was stirred for 1 hour.

The reaction mixture was concentrated under a reduced pressure at low temperature and the residue was dissolved in 50 ml. of cold water. The solution was adjusted to pH 2 with 10% hydrochloric acid, and the precipitates which had formed were extracted twice each time with 10 ml. of ethyl acetate. The ethylacetates extracts were combined, washed with an 5% aqueous solution of sodium chloride, and dried over anhydrous magnesium sulfate. To the ethyl acetate solution was added a 30% n-butanol solution of sodium 2-ethylhexanoate until no further precipitate which had formed, and the precipitates formed were recovered by filtration. By re-precipitating the precipitates from a mixture of ether and methanol, 0.36 g. of light yellow powdery crystals of sodium 6-[D-2-(2,4-dihydroxypyrimidine-5-carbonylamino)-2-(1,4-cyclohexadien-1-yl)acetamido]penicillanate was obtained.

Melting point 230°–237°C. (decomp.)

Infrared absorption spectra: $\nu_{max\ KBr}$ cm$^{-1}$: 3400, 3250 (OH, NH), 1770 (β-lactam), 1660 (amide), 1605 (carboxylate).

Nuclear magnetic resonance spectra (D$_2$O):

δ: 1.34, 1.43  (6H, 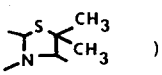 )

2.57  (4H, s, 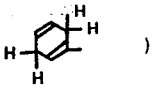 )

4.15  (1H, s, 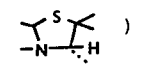 )

4.90  (1H, s, 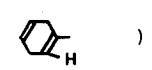 )

5.40  (2H, q, 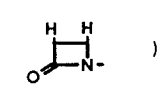 )

5.62  (2H, s, 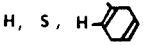 )

5.87  (1H, s, 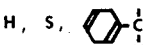 )

8.51  (1H, s, 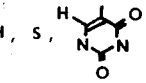 )

EXAMPLE 17

In 10 ml. of ice water was suspended 1 g. of epicillin and then 2N-sodium hydroxide solution was added to the suspension until the pH become 9, accompanied by stirrng to dissolve epicillin. While cooling the solution in a ice bath, 380 mg. of thiophene-2-carbonyl chloride was added to the solution and then 2 N-sodium hydroxide solution was added dropwise slowly to the mixture and the mixture was maintained at a pH of 8.5–9.5 for 30 minutes.

To the reaction mixture was added 20 ml. of methyl isobutyl ketone and the mixture was adjusted to pH 2 with 2N-hydrochloric acid with stirring. The organic layer which had formed was separated and dried over anhydrous magnesium sulfate. To the solution was added a 30% n-butanol solution of sodium 2-ethylhexanoate until no further precipitates which had formed and the precipitates formed were recovered by filtration, washed with ether, and dried under reduced pressure.

Thus, 0.75 g. of light brown powdery cyrstals of sodium 6-[D-2-(thiophene-2-carbonylamino)-2-(1,4-cyclohexadien-1-yl)-acetamido]penicillanate was obtained.

Melting point 215°–220°C. (decomp.)

Infrared absorption spectra: $\nu_{max}^{KBr}$cm$^{-1}$: 3350 (NH), 1770 (β-lactam), 1660 (amide), 1620 (carboxylate).

Nuclear magnetic resonance spectra (D$_2$O):

δ: 1.34, 1.39  (6H, 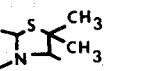 )

2.50  (broad, 4H, 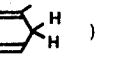 )

4.10  (1H, s, 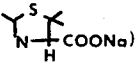 )

5.20–5.75  (6H, broad,  )

6.88  (1H, q, 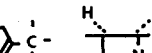 )

7.37  (1H, d, 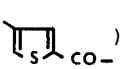 )

7.57  (1H, d, 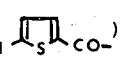 )

EXAMPLE 18

A mixture of 1 g. of epicillin, 0.5 g. of anhydrous magnesium sulfate, 0.7 ml. of triethylamine, 5 ml. of hexamethylphosphoramide, and 25 ml. of dichloromethane was stirred for 30 minutes at room temperature and then magnesium sulfate was filtered off to provide a dichloromethane solution of epicillin triethylamine salt.

The solution was cooled to −20°C, 0.4 g. of coumalyl chloride and 0.4 ml. of triethylamine were added to the solution, and after stirring the mixture for 2 hours at the same temperature, dichloromethane was distilled off from the reaction mixture under reduced pressure.

The residue was dissolved in 25 ml. of cold water, 25 ml. of ethyl acetate was added to the solution in layer, and after adjusting the pH to 2 with 10% hydrochloric acid, the ethyl acetate layer which had formed was separated. The ethyl acetate solution was washed with a 5% aqueous solution of sodium chloride and dried over anhydrous magnesium sulfate. To the solution was added a 30% n-butanol solution of sodium 2-ethylhexanoate until no further precipitates which had formed. The precipitates formed were recovered by filtration and re-precipitated from a mixture of methanol and ether to provide 0.4 g. of the light brown powdery crystal of sodium 6-[D-2-(coumalylamino)-2-(1,4-cyclohexadien-1-yl)acetamido]-penicillanate.

Melting point above 300°C. (decomp.).

Infrared abosprion spectra:

$\nu_{max}^{KBr}$ cm$^{-1}$: 3420, 3300 (OH, NH), 1765 ($\beta$-lactam), 1660–1640 (amide), 1600 (carboxylate).

Nuclear magnetic resonance spectra (D$_2$O):

δ: 1.37, 1.43   (6H, 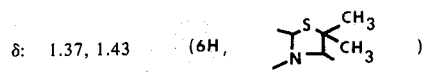 )

2.58   (4H, s, 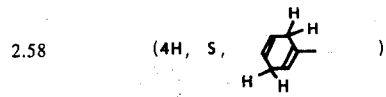 )

4.09   (1H, s, 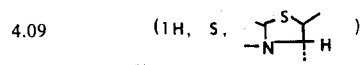 )

5.02   (1H, s, 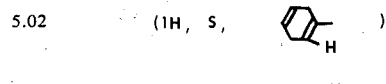 )

5.41   (2H, q, 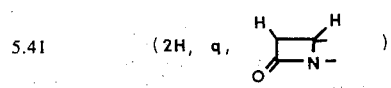 )

5.61   (2H, s, 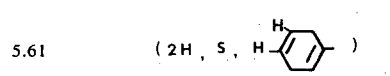 )

5.81   (1H, s, 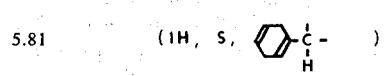 )

6.30   (1H, d, 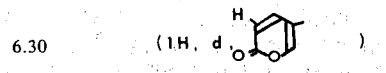 )

7.82   (1H, q, 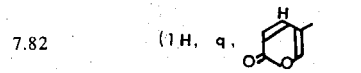 )

8.12   (1H, d, 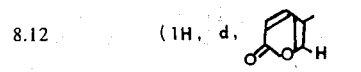 )

EXAMPLE 19

A mixture of 1 g. of epicillin, 0.5 g. of anhydrous magnesium sulfate, 0.7 ml. of triethylamine, and 25 ml. of dichloromethane was stirred for 30 minutes at room temperature and then magnesium sulfate was filtered off to provide a dichloromethane solution of epicillin triethylamine salt.

In 10 ml. of hexamethylphosphoramide amide was suspended 0.65 g. of 1-ethyl-6-nitro-4-quinolone-3-carboxylic acid and then 0.4 ml. of triethylamine was added to the suspension. To the mixture was added dropwise 2 ml. of a dichloromethane solution of 0.25 ml. of ethyl chlorocarbonate at 0°–5°C. and the mixture was stirred for one hour at the same temperature. To the resulting solution was added dropwise the dichloromethane solution of epicillin triethylamine salt prepared above at temperatures of from −20°C. to −30°C. and the mixture was stirred for 1 hour. The reaction mixture was concentrated under reduced pressure at low temperature and the residue was dissolved in 50 ml. of cold water. The solution was then adjusted to pH 2 with 10% hydrochloric acid and the precipitates which had formed were recovered by filtration and washed with water. The precipitates were dissolved in 50 ml. of a mixture of n-butanol and ethyl acetate of 1:4 by volume ratio and a small amount of insoluble materials were filtered off. The filtrate was washed with an 5% aqueous solution of sodium chloride and dried over anhydrous magnesium sulfate. Then, a 30% n-butanol solution of sodium 2-ethylhexanoate was added to the filtrate until no further precipitates formed and after adding thereto 50 ml. of ether followed by stirring, the precipitates were recovered by filtration.

By re-precipitating the precipitates from a mixture of methanol and ether, 0.45 g. of the light yellow-brown powdery crystals of sodium 6-[D-2-(1-ethyl-6-nitro-4-quinolone-3-carbonylamino)-2-(1,4-cyclohexadien-1-yl)acetamido]penicillanate was obtained.

Melting point 217°–220°C. (decomp.)

Infrared absorption spectra: $\nu_{max}^{KBr}$cm$^{-1}$: 3400, 3200 (OH, NH), 1770 ($\beta$-lactam), 1660–1640 (amide), 1610 (carboxylate).

Nuclear magnetic resonance spectra (D$_2$O):

δ: 1.22   (3H, t, CH$_3$—CH$_2$—N<) 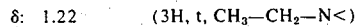

1.32, 1.41   (6H, 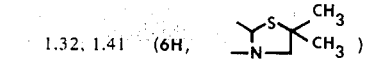 )

-continued

| | | |
|---|---|---|
| 2.57 | (4H, s, | 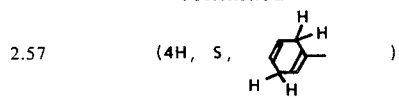 ) |
| 4.00 | (2H, q, CH₃—CH₂—N<) | |
| 4.08 | (1H, s, | 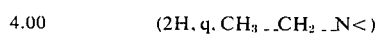 ) |
| 4.83 | (1H, s, | 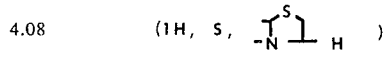 ) |
| 5.38 | (2H, q | 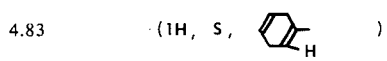 ) |
| 5.60 | (2H, s, | 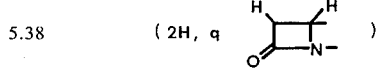 ) |
| 5.90 | (1H, d, | 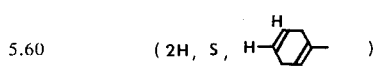 ) |
| 7.39 | (1H, d, | 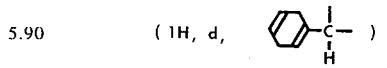 ) |
| 7.94 | (1H, d, | 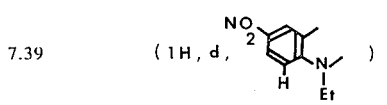 ) |
| 8.20 | (1H, s, | 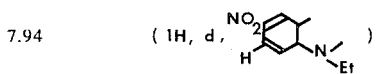 ) |
| 8.40 | (1H, s, | 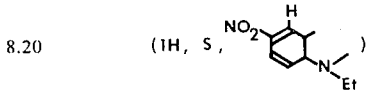 ) |

EXAMPLE 20

In 20 ml. of ice water was suspended 1 g. of epicillin and then 25 ml. of 1-N-sodium hydroxide solution was added to the suspension with stirring to dissolve epicillin. After adding to the solution 0.55 g. of 4-chloro-3-nitrobenzoyl chloride with stirring while cooling to 0°–5°C., 1 N-sodium hydroxide solution was added dropwise little by little to the mixture and the mixture was maintained at a pH of 8–8.5 for 30 minutes.

To the reaction mixture was added 30 ml. of ethyl acetate in layer and the pH was adjusted to 2 with 10% hydrochloric acid with stirring. The ethyl acetate layer was separated, washed with an 5% aqueous solution of sodium chloride, and dried over anhydrous magnesium sulfate.

Then, 1.5 ml. of a 30% n-butanol solution of sodium 2-ethylhexanoate was added to the solution and then 30 ml. of ether was added thereto. The white precipitates which had formed were recovered by filtration, washed with ether, and dried to provide 0.95 g. of white powdery cyrstals of sodium 6-[D-2-(4-chloro-3-nitrobenzoylamino)-2-(1,4-cyclohexadien-1-yl)acetamido]-penicillanate.

Melting point 204°–206°C. (decomp.)

Infrared absorption spectra: $\nu_{max}^{KBr}$cm⁻¹: 3350 (broad) (OH, NH), 1765 (β-lactam), 1660 (amide), 1605 (carboxylate).

Nuclear magnetic resoance spectra (D₂O):

| δ: | | | |
|---|---|---|---|
| 1.35, 1.39 | (6H, | 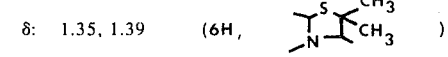 ) |
| 2.50 | (4H, s, | 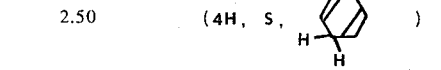 ) |
| 4.07 | (1H, s, | 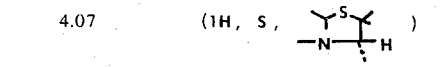 ) |
| 5.12 | (1H, s, | 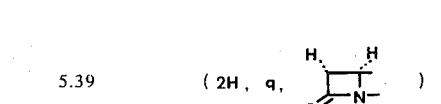 ) |
| 5.39 | (2H, q, |  ) |
| 5.45 | (2H, s, |  ) |
| 5.73 | (1J, s, |  ) |
| 7.30 | (1H, d |  ) |
| 7.77 | (1H, d, | 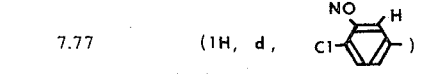 ) |
| 8.07 | (1H, d, |  ) |

EXAMPLE 21

In 10 ml. of ice water was suspended 1 g. of 6-[D-2-amino-2-(1,4-cyclohexadien-1-yl)acetamido]penicillanic acid and then 2N-sodium hydroxide solution was added to the suspension until the pH reached 9 to dissolve the penicillanic acid. After adding to the solution 350 mg. of furan-2-carbonyl chloride while ice-cooling, 2N-sodium hydroxide solution was added slowly dropwise to the solution and the mixture was maintained at a pH of 8.5–9.5 for 30 minutes.

To the reaction mixture was added 20 ml. of methyl isobutyl ketone and the mixture was adjusted to pH 2 with 2 N-hydrochloric acid with stirring. The organic layer was separated and dried over anhydrous magnesium sulfate. To the solution was added dropwise a 30% n-butanol solution of sodium 2-ethylhexanate until no further precipitate formed. The precipitates were recovered by filtration, washed with ether, and dried under reduced pressure to provide 0.4 g. of light yellow powdery crystals of sodium 6-[D-2-(furan-2-carbonylamino)-2-(1,4-cyclohexadien-1-yl)acetamido]-penicillanate.

Melting point 215°–225°C. (decomp.)

Infrared absorption spectra: $\nu_{max}^{KBr} cm^{-1}$: 3400 (—NH), 1765 ($\beta$-lactam), 1640 (amide), 1600 (carboxylate)

Nuclear magnetic resonance spectra ($D_2O$):

δ: 1.55, 1.62 (6H, 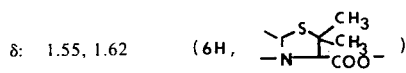)

2.70 (broad, 4H, )

4.27 (s, 1H, 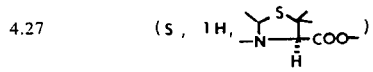)

5.20 (s, 1H, 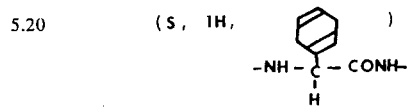)

5.58–5.66 (m, 4H, 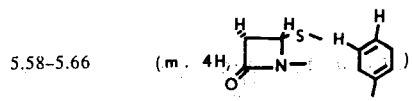)

5.95 (broad, 1H, 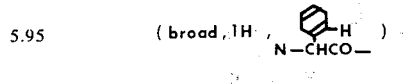)

6.60 (q, 1H, 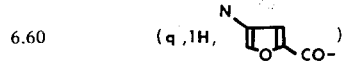)

7.23 (dd, 1H, )

7.65 (d, 1H, 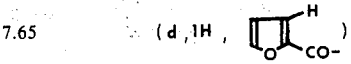)

EXAMPLE 22

(a) In 30 ml. of methylene chloride were dissolved 2.26 g. of benzylpenicillin phenacyl ester and 2.06 ml. of N,N-dimethylaniline and then after adding to the solution 1.15 g. of phosphorus pentachloride at −25°C, the mixture was stirred for 1.5 hours at the same temperature. Then, 20 ml. of methanol was added to the solution at the same temperature followed by stirring for 2.5 hours to form a solution of iminoether.

Separately, 1.88 g. of DL-p-hydroxyphenyl-α-(4-oxo-4H-thiopyran-3-yl-carboxyamido)acetic acid and 0.80 ml. of N,N-dimethylaniline were dissolved in a mixture of 4 ml. of dimethylformamide and 8 ml. of methylene chloride. After cooling the solutin to temperatures of from −50°C. to −10°C., 0.58 ml. of ethyl chlorocarbonate was added to the solution and the mixture was stirred for 30 minutes to provide a solutin of a mixed acid anhydride. The solution was cooled to −25°C. and was then added to a mixture of the solution of the iminoether prepared above, and 3.43 ml. of N,N-dimethylaniline.

After maintaining the mixture at −25°C. for 2 hours, 50 ml. of water and 100 ml. of methylene chloride were added to the mixture and after shaking sufficiently the mixture, the organic layer was separated. The organic layer solution thus recovered was washed with an aqueous solution of sodium chloride, acidified with hydrochloric acid and a 5% aqueous solution of of sodium bicarbonate and then dried over anhydrous magnesium sulfate. Then, the organic solvent was distilled off under a reduced pressure from the reaction mixture, the oily residue obtained was dispersed in 100 ml. of ether to form a powder. The powder was recovered by filtration, washed with ether, and dried to provide 2.4 g. of DL-6-{p-hydroxyphenyl-α-(4-oxo-4H-thipyran-3-yl-carboxamido)acetamido}-penicillanic acid phenacyl ester.

Infrared absorption spectra: $\nu_{max}^{KBr} cm^{-1}$: 1780 ($\beta$-lactam), 1760 (—COO—), 1695 (—CC—), 1655 (amide).

Nuclear magnetic resonance spectra ($D_6$-DMSO):

δ: 1.54, 1.59, 1.65, 1.70 (6H, )

4.44, 4.47 (1H, )

5.64 (—$CH_2$—) 

5.44–5.81 (3H, m, 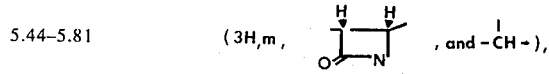, and —CH—), 6.74, 7.18 (d, 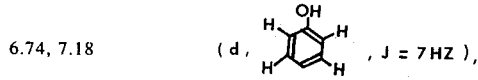, J = 7HZ), 7.20 (d, 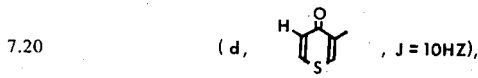, J = 10HZ), near 7.60 (3H, m, —CO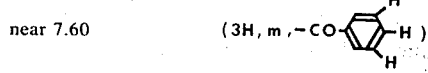)

near 7.96 (2H — CO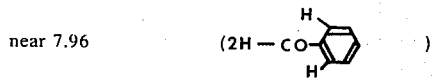)

8.36 (dd, 1H, 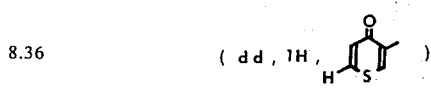)

9.22 (1H, —CONH—), 9.30 (d, , J = 4HZ), 10.61 (1H, —CONH—)

Preparation of the starting material:

In a mixture of 50 ml. of water and 10 ml. of dioxane was suspended 3.0 g. of DL-α-amino-p-hydroxyphenylacetic acid and then 4 N-sodium hydroxide solution was added to the suspension to provide a solution of pH 10–11. After cooling the solution to 0°–5°C. with stirring, 3.5 g. of 4-oxo-4H-thiopyran-3-carbonyl chloride was added to the solution and then 4 N-sodium hydroxide solution was added to maintain the pH at 9–10 for 3 hours. The solution was adjusted to pH 2 with 6N-hydrochloric acid and the brown viscous material thus liberated was successively extracted with 50 ml., 20 ml, and then 15 ml. of n-butanol. The extracts were combined, washed with an aqueous solution of sodium chloride acidified with hydrochloric acid, and dried over anhydrous magnesium sulfate. The solvent was distilled off under reduced pressure from the reaction mixture and a small amount of ether was added to the residue which was obtained to form crystals, were recovered by filtration to provide 4.9 g. of DL-p-hydroxyphenyl-α-(4-oxo-4H-thiopyran-3-yl-carboxamido)acetic acid.

Infrared absorption spectra: $\nu_{max}^{KBr}$cm$^{-1}$: 1710 (—COOH), 1640 (—CONH—).

Nuclear magnetic resonance spectra (100 MHZ, D$_6$-DMSO)

δ: 5.38 (d, —CH—, J = 7 HZ)

6.77 7.20 (d, 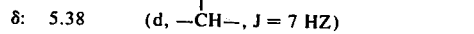, J = 9HZ)

7.22 (d, 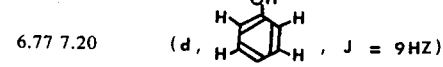, J = 8HZ)

8.40 (dd, 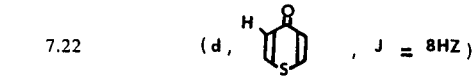)

9.34 (d, 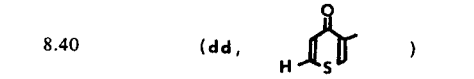, J = 5HZ)

9.50 (1H, —COOH)

10.59 (d, —CONH—, J = 7 HZ).

b. In 30 ml. of methylene chloride were dissolved 2.26 g. of benzylpenicillin phenacyl ester and 2.06 ml. of N,N-dimethylaniline and after cooling the solution to −25°C. and adding thereto 1.15 g. of phosphorus pentachloride, the mixture was stirred for 1.5 hours at the asme temperature. Then, 20 ml. of methanol was added to the mixture and the resultant mixture was further stirred for 2.5 hours to form an iminoether solution.

Separately, in a mixture of 4 ml. of dimethylformamide and 8 ml. of methylene chloride were dissolved 1.88 g. of D(-)-p-hydroxyphenyl-α-(4-oxo-4H-thiopyran-3-yl-carboxamido)acetic acid and 0.08 ml. of N,N-dimethylaniline and then after further adding 0.58 ml. of ethyl chlorocarbonate to the solution at −10°C. ± 3°C., the mixture was stirred for 35 minutes to form a solution of a mixed acid anhydride. The resultant solution was cooled to −25°C. there was added thereto 3.43 ml of N,N-dimethylaniline. The iminoether solution prepared above was added at once. After maintaining the mixture at temperature of from −20°C. to −25°C. for 2 hours, 30 ml. of water and 20 ml. of methylene chloride were added thereto. the resultant mixture was shaken sufficiently, and the precipitates, which formed were recovered by filtration.

The precipitate was identified a the starting material, D(-)-p-hydroxyphenyl-α-(4-oxo-4H-thiopyran-3-yl-carboxamido)acetic acid, from the infrared absorption spectra and the nuclear magnetic resonance spectra of the authentic sample. The organic layer was separated, washed with an aqueous solution of sodium chloride acidified with hydrochloric acid and then a 5% aqueous solution of sodium bicarbonate followed by drying over anhydrous magnesium sulfate. The organic solvent was distilled off under reduced pressure and the oily residue was dispersed in 50 ml. of ether to form a powder. The powder was recovered by filtration to provide 1.6 g. of D(-)-6-{p-hydroxyphenyl-α-(4-oxo-4H-thiopyran-3-yl-carboxamido)acetamido}penicillanic acid phenacyl ester.

Infrared absorption spectra: $\nu_{max}^{KBr}$cm$^{-1}$: 1780 (β-lactam), 1760 (—COO—),

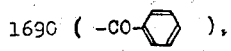

1665 (amide).

Nuclear magnetic resonance spectra (D$_6$-DMSO ppm):

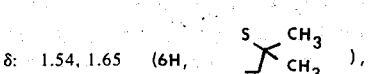

δ: 1.54, 1.65 (6H, S×CH$_3$/CH$_3$), 4.45 (1H, S, ),

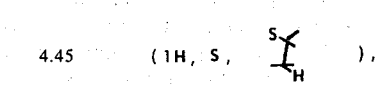

5.45–5.70 (2H, m, ),

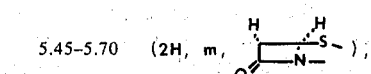

5.65 (—COOCH$_2$—),

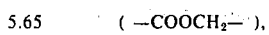

5.77 (d, —CH—, J = 7HZ), 6.56, 7.25 (d, 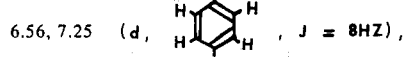, J = 8HZ), 7.23 (d, 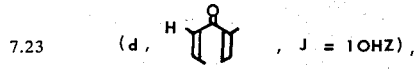, J = 10HZ), near 7.6 (m, —CO— 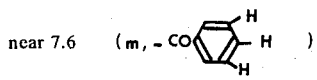 )

near 8.0 (m, —CO— 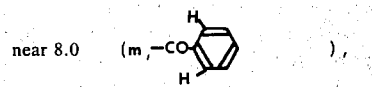 ), 8.39 (dd, 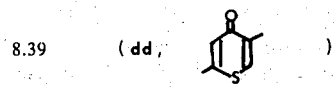 )

9.24 (1H, —CONH—), 9.34 (d, 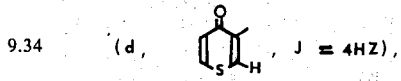, J = 4HZ), 10.66 (d, —CONH—, J = 7HZ).

Preparation of the starting material:

In 72 ml. of a cooled aqueous solution of 2N-sodium hydroxide was dissolved 8.0 g. of D(-)-α-amino-p-hydroxyphenylacetic acid and then 9.3 g. of 4-oxo-4H-thiopyran-3-carbonyl chloride was slowly added to the solution at 0°–5°C. over a period of about 2 hours. The mixture was further stirred for 30 minutes at the same temperature. The brown reaction mixture obtained was adjusted to pH 2 with 6N-hydrochloric acid followed by stirring for one hour. The resulting crystalline powder thus obtained was recovered by filtration, washed with water, and dried over phosphorous pentoxide under reduced pressure. By recrystallizing the product from water-containing dimethylformamide, 11.7 g. of D(-)-p-hydroxyphenyl-α-(4-oxo-4H-thiopyran-3-yl carboxamido)acetic acid was obtained.

[α]$_D^{25}$ = −130.5 (C = 1, dimethylsulfoxide)

Infrared absorption spectra: $\nu_{max}^{KBr}$cm$^{-1}$: 1730 (—COOH), 1630 (—CONH—).

Nuclear magnetic resonance spectra (D$_6$-DMSO, ppm.):

δ: 5.36 (d, —CH—, J = 7HZ), 6.78, 7.20 (d, 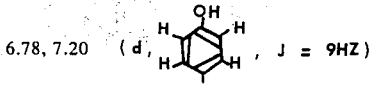, J = 9HZ)

| | | |
|---|---|---|
| 7.20 | (d, 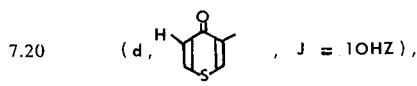, J = 10HZ), | |
| 8.38 | (dd, 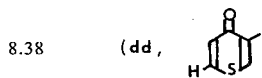) | |
| 9.34 | (d, 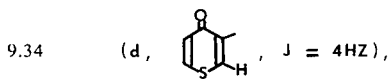, J = 4HZ), | |
| 9.50 | (1H, —COOH), | |
| 10.58 | (d, —CONH—, J = 7HZ) 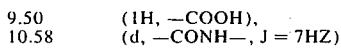 | | c. In 2 D(-)-of dimethylformamide was dissolved 1.0 g. of D(-0-6-{p-hydroxyphenyl-α-(4-oxo-4H-thiopyran-3-yl carboxamido)acetamido}penicillanic acid phenacyl ester and then after adding to the solution 425 mg. of sodium thiophenlate, the mixture was stirred for 2 hours at room temperature. After adding 10 ml. of ice water to the reaction mixture and then adjusting the pH thereof to 7 with 6N-hydrochloric acid, the aqueous layer was extracted with 10 ml. of ethyl acetate. The aqueous layer was further adjusted to pH 2 with 6N-hydrochloric acid and then extracted three times each with 10 ml. of a mixture of ethyl acetate and sec-butanol of 7 : 1 by volume ratio. The extracts were combined, washed with 20% aqueous solution of sodium chloride, and dried over anhydrous magnesium sulfate. The organic solvent solution was concentrated under reduced pressure and the oily residue was crystallized by adding a small amount of ethyl acetate. Then, ethylacetate and ether were further added thereto and the crystals which had formed were recovered by filtration to provide 0.6 g. of D(-)-6-{p-hydroxyphenyl-α-(4-oxo-4H-thiopyran-3-yl-carboxamido)-acetamido}penicillanic acid.

Nuclear magnetic resonance spectra (D₆-DMSO, ppm.):

| | | |
|---|---|---|
| δ: 1.44, 1.58 | (6H, 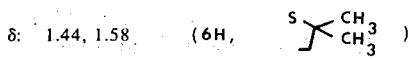) | |
| 4.21 | (1H, S, 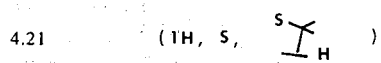) | |
| 5.38–5.67 | (2H, m; 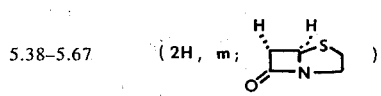) | |
| 5.78 | (1H, d, J = 8HZ, 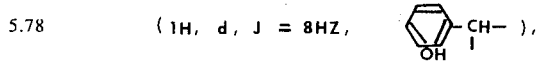) | |
| 6.78, 7.26 | (4H, d, J = 8HZ, 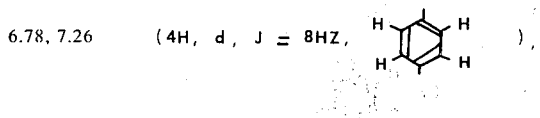) | |

| | | |
|---|---|---|
| 7.22 | (1H, d, J = 8HZ, 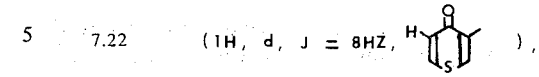), | |
| 8.37 | (1H, dd, J = 10, 5HZ, 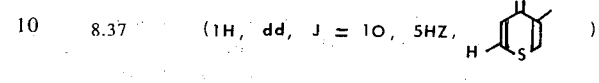) | |
| 9.18 | 1(H, d, NH), | |
| 9.36 | (1H, d, J = 5HZ, 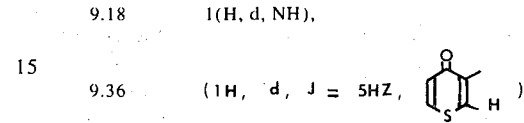) | |
| 10.65 | (1H, d, J = 8HZ). | |

The product coincided with the authentic sample obtained by the reaction of D(-)-α-amino-p-hydroxyphenylacetamidopenicillanic acid and 4-oxo-4H-thiopyran-3-carbonyl chloride in thin layer chromatography, infrared absorption spectra, and nuclear magnetic resonance spectra.

EXAMPLE 23

In 30 ml. of methylene chloride were suspended 1.86 g. of benzylpenicillin potassium and 2.06 ml. of N,N-dimethylaniline and after further adding to the suspension 0.4 ml. of phosphorus trichloride at 0°–5°C. and stirring the mixture for 30 minutes, a clear solution was obtained. The solution was cooled to −25°C. and after adding thereto 1.2 g. of phosphorus pentachloride, the mixture was stirred for 1.5 hours at the same temperature. Then, 20 ml. of methanol and 1.05 ml. of triethylamine were added dropwise to the mixture at the same temperature and the resultant mixture was stirred for 2.5 hours to provide an iminoether solution.

Separately, in a mixture of 4 ml. of dimethylformamide and 8 ml. of methylene chloride were dissolved 1.83 g. of D(-)-p-hydroxyphenyl-α-(4-oxo-4H-thiopyran-3-carboxamido)acetic acid and 0.78 ml. of N,N-dimethylaniline and after cooling the solution to −5°C. ± 5°C. and adding thereto 0.58 ml. of ethyl chlorocarbonate, the resultant mixture was stirred for 35 minutes to provide a solution of a mixed acid anhydride. The solution was cooled to −25°C. and to the solution was added the iminoether solution prepared above after these had been added thereto 3.43 ml. of dimethylaniline. After stirring the mixture for 2 hours, 30 ml. of water was added thereto, the mixture was sufficiently shaken, and the organic layer was separated. The aqueous layer was further extracted with 30 ml. of methylene chloride. The organic solution was combined with the extract and the mixture was concentrated under reduced pressure. The oily residue was added to a mixture of 50 ml. of a saturated solution of sodium bicarbonate and 30 ml. of ethyl acetate and the aqueous layer was separated. To the aqueous solution was added 40 ml. of a mixture of ethyl acetate and sec.-butanol of 7 : 1 by volume ratio in layer, the pH thereof was adjusted to 2 with 6N-hydrochloric acid, and then the organic layer was separated. The organic solution was washed with a 20% aqueous solution of sodium chloride, and dried over anhydrous magnesium sulfate. The organic solvent was distilled off under reduced pressure at temperatures lower than 40°C. and the residue was crystallized by adding thereto a small amount of ethyl acetate. A mixture of ethyl acetate and ether was further added to the crystalline residue and then the crystals were recovered by filtration to provide 0.8 g. of D(-)-6-{p-hydroxyphenyl-α-(4-oxo-4H-thiopyran-3-yl-carboxamido)acetamido}penicillanic acid.

EXAMPLE 24 a. In 30 ml. of methylene chloride was dissolved 2.0 g. of benzylpenicillin phenacyl ester and after adding to the solution 1.84 ml. of dimethylaniline and then 1.11 g. of phosphorus pentachloride at −25°C., the mixture was stirred for 2 hours at the same temperature. To the reaction mixture was added 15 ml. of methanol at −25°C. followed by stirring for further 2 hours and then 1.51 ml. of dimethylaniline was added to the mixture.

Separately, 1.75 g. of D(-)-p-hydroxyphenyl-α-(4oxo- 4H-thiopyran-3-ylcarboxamido)acetic acid was dissolved in 15 ml. of a mixture of dimethylformamide and methylene chloride of 1 : 1 by volume ratio, then 550 mg. of N-methylmorpholine was added to the solution, and after cooling the mixture to −5°C. and adding thereto 622 mg. of ethyl chlorocarbonate, the mixture was stirred for 30 minutes at the same temperature. To the resultant mixture was added dropwise the reaction mixture prepared above at −25°C. and the mixture was stirred for 3 hours at the same temperature.

The reaction mixture was washed successively with 60 ml. and 40 ml of ice water and, washed further with a diluted aqueous solution of sodium bicarbonate and then water, and then an organic layer which had formed was separated. The organic solution was dried over anhydrous magnesium sulfate and the solvent was distilled off under reduced pressure. The residue was washed with petroleum ether and crystallized from a mixture of methylene chloride and ether. The crystals were recovered by filtration, washed with ether and dried to provide 2.15 g. of D(-)-6-{p-hydroxyphenyl-α-(4-oxo-4H-thiopyran-3-ylcarboxamido)acetamido}penicillanic acid phenacyl ester (hereinafter, the ester is called ester (A)). Furthermore, the filtrate was applied to a silica gel column chromatography and 166 mg. of ester (A) was obtained. The structure of the product determined by the infrared absorption spectra and the nuclear magnetic resonance spectra coincided with the structure described above.

$[\alpha]_D^{25} = +149$ (C = 1, dimethylsulfoxide)

b. In 4.8 ml. of dimethylformamide was dissolved 1.5 g. of ester (A) and after adding to the solution 657 mg. of sodium thiophenolate, the mixture was stirred for 15 minutes at room temperature. To the reaction mixture was added 120 ml. of acetone followed by stirring for about 10 minutes and white precipitates which had formed were recovered by filtration. The precipitates were dissolved in 50 ml. of water, the solution was adjusted to pH 2 with 10% hydrochloric acid, and the white precipitates which had formed were recovered by filtration. The precipitates were dissolved in a mixture of ethyl acetate and sec-butanol of 8 : 1 by volume ratio and the solution was washed with water and dried over anhydrous magnesium sulfate. The solvent was distilled off under reduced pressure and to the residue thus formed there was added ether, whereby 870 mg. of white precipitates of D(-)-6-{p-hydroxyphenyl-α-(4-oxo-4H-thiopyran-3-ylcarboxamido)acetamido}penicillanic acid were obtained.

The structure of the product determined by the infrared absorption spectra and the nuclear magnetic resonance spectra coincided with the structure described above.

EXAMPLE 25

In 8 ml. of a mixture of dimethylformamide and methylene chloride of 1 : 1 by volume ratio was dissolved 1 g. of α-(p-hydroxyphenyl)-α-(4-oxo-4H-thiopyran-3-ylcarboxamido)acetic acid and then 0.342 ml. of N-methylmorpholine was added to the solution. The mixture was cooled to −5°C., and 0.311 ml. of ethyl chlorocarbonate was further added to the mixture followed by stirring for 30 minutes.

To the reaction mixture was added 20 ml. of a methylene chloride solution containing 1.1 g. of 6-aminopenicillanic acid phenacyl ester at −30°C. and the mixture was stirred for 2 hours. The reaction mixture was washed twice each time with an aqueous solution of sodium bicarbonate, water, diluted hydrochloric acid, and then water, and dried over anhydrous magnesium sulfate. The solvent was removed under reduced pressure and the residue which had formed was crystallized from a mixture of methylene chloride and ether to provide 1.01 g. of 6-{α-(p-hydroxyphenyl)-α-(4-oxo-4H-thiopyran-3-ylcarboxamido)acetoamido}penicillanic acid phenacyl ester (hereinafter, the ester is called ester (A′)).

Furthermore, by subjecting the mother liquor to a silica gel column chromatography, 554 mg. of ester (A′) was obtained.

The structure of the product determined by the infrared absorption spectra and the nuclear magnetic resonance spectra coincided with the structure described above.

EXAMPLE 26

In a mixture of 10 ml. of water and 5 ml. of dioxane was suspended 1 g. of 6-aminopenicillanic acid and after adjusting the pH thereof to 8.6–8.8 with 1N aqueous sodium hydroxide solution, the mixed acid anhydride prepared from 1.55 g. of α-(p-hydroxyphenyl)-α-(4-oxo-4H-thiopyran-3-ylcarboxamido)acetic acid, 0.530 ml. of N-methylmorpholine, and 0.483 ml. of ethyl chlorocarbonate was added thereto at temperatures of 0°–2°C. followed by stirring for 1 hour at the same temperature.

The reaction mixture was filtered, the filtrate was adjusted to pH 2 and the product was extracted with 50 ml. and then 40 ml. of a mixture of ethyl acetate and sec-butyl alcohol of 8 : 1 by volume ratio. The extract thus obtained was washed twice each time with 30 ml. of water, dried over anhydrous magnesium sulfate, and concentrated under reduced pressure. By adding ether to the residue which had formed, 820 mg. of a yellowish powder of 6-{α-(p-hydroxyphenyl)-α-(5-oxo-4H-thiopyran-3-ylcarboxamido)acetamido}penicillanic acid (hereinafter, it is called ester (B)) was obtained.

By crystallizing the product from a mixture of isopropyl alcohol and methylene chloride, ester (B) was obtained. The structure of the product determined by the infrared absorption spectra and the nuclear magnetic resonance spectra coincided with the aforesaid structure of ester (B).

EXAMPLE 27

In 50 ml. of isopropanol was suspended 4.7 g. of D(-)-6-[p-hydroxyphenyl-α-(4-oxo-4H-thiopyran-3- ylcarboxamido)acetamido]-penicillanic acid and then 25 ml. of water was added to the suspension to dissolve the penicillanic acid. To the solution was further added gradually 85 ml. of water with stirring at room temperature and the mixture was stirred, whereby a crystals were formed. Then, after further adding 90 ml. of water slowly to the system, the mixture was allowed to stand still under ice cooling to form sufficiently the crystals.

The crystals were recovered by filtration, washed with a mixture of isopropanol and water of 1 : 4 by volume ratio, and dried by passing air to provide 4.2 g. of white crystals of D(-)-6-[p-hydroxy-phenyl-α-(4-oxo-4H-thiopyran-3-ylcarboxamido)acetamido]-penicillanic acid di-hydrate at a yield of 83%.

Melting point about 175°C. (decomp.).
$[\alpha]_D^{20} = +148°$ (C = 1, dimethylformamide)
Infrared absorption spectra: $\nu_{max}^{KBr}$cm$^{-1}$: 1790, 1780 (shouldler), 1745, and 1640.
Elemental analysis for $C_{22}H_{21}N_3O_7S_2 \cdot 2H_2O$:

|  | C | H | N | S |
|---|---|---|---|---|
| Calculated: | 48.97% | 4.67% | 7.79% | 11.88% |
| Found: | 49.04% | 4.43% | 7.64% | 11.67% |

EXAMPLE 28

In 8 ml. of acetone containing 20% water was dissolved 2.0 g. of D(-)-6-[p-hydroxyphenyl-α-(4-oxo-4H-thiopyran-3-ylcarboxamido)-acetamido]penicillanic acid and after adding to the solution 20 ml. of water, the mixture was stirred at room temperature, whereby crystals formed. Then, 20 ml. of water was further added to the system, the mixture was stirred under ice cooling to form sufficiently crystals, and the crystals were recovered by filtration, washed with water, and dried by passing air at 80°C. for 5 hours to provide 1.78 g. of crystalline D(-)-6-[p-hydroxyphenyl-α-(4-oxo-4H-thiopyran-3-ylcarboxamido)acetamido]penicillanic acid di-hydrate at a yield of 83%.

Melting point about 175°C. (decomp.)
$[\alpha]_D^{20} = +149°$ (C = 1, dimethylformamide)
Infrared absorption spectra: $\nu_{max}^{KBr}$cm$^{-1}$: 1790, 1780 (shoulder), 1745, and 1640.

EXAMPLE 29

In 6 ml of a mixture of methanol, acetone, and water of 4 : 4 : 2 by volume ratio was dissolved 2.0 g. of D(-)-6-[p-hydroxyphenyl-α-(4-oxo-4H-thiopyran-3-ylcarboxamido)acetamido]penicillanic acid and after adding to the solution 20 ml. of water, the mixture was stirred at room temperature whereby crystals formed.

Then, 20 ml. of water was further added to the system followed by stirring under ice cooling to form sufficiently the cyrstals. The crystals were recovered by filtration, washed with water, and dried by passing air for 5 hours at 80°C. to provide 1.77 g. of crystalline D(-)-6-[p-hydroxyphenyl-α-(4-oxo-4H-thiopyran-3-ylcarboxamido)-acetamido]penicillanic acid di-hydrate at a yield of 82.6%.

Melting point about 175°C. (decomp.)
$[\alpha]_D^{20} = +147°$ (C = 1, dimethylformamide)
Infrared absorption spectra: $\nu_{max}^{KBr}$cm$^{-1}$: 1790, 1780 (shoulder), 1745, 1640.

EXAMPLE 30

In 5 ml. of a mixture of methanol, methylene chloride, and water of 9 : 9 : 2 by volume ratio was dissolved 2.0 g. of D(-)-6-[p-hydroxyphenyl-α-(4-oxo-4H-thiopyran-3-ylcarboxamido)acetamido]penicillanic acid and after adding to the solution 10 ml. of water, the mixture was stirred at room temperature to form crystals. Then, 5 ml. of water was further added thereto and the mixture was stirred under ice cooling to form sufficiently the crystals. The crystals were recovered by filtration, washed with water, and dried by passing air for 5 hours at 80°C. to provide 1.96 g. of crystalline D(-)-6-[p-hydroxyphenyl-α-(4-oxo-4H-thiopyran-3-ylcarboxamido)acetamido]penicillanic acid di-hydrate at a yield of 91%.

Melting point about 175°C. (decomp.)
$[\alpha]_D^{20} = +148°$ (C = 1, dimethylformamide)
Infrared absorption spectra: $\nu_{max}^{KBR}$cm$^{-1}$: 1790, 1780 (shoulder), 1745, 1640.

EXAMPLE 31

After dissolving 16.7 g. of sodium bicarbonate in 350 ml. of distilled water for injection, 100 g. of D(-)-6-{α-(p-hydroxyphenyl)-α-(4-oxo-4H-thiopyran-3-yl-carboxamido)acetamido}penicillanic acid was dissolved in the solution with sufficient stirring. Thereafter, a small amount of distilled water for injection was added to make the whole volume 500 ml. The solution was filtered by means of a membrane filter for sterilizing. The solution was filled into vials 5 ml. per vial and subjected to lyophilization. Then, each vial was sealed tightly with a rubber stopper and then closed with an aluminum cap.

The product in the form of an injectable solution is prepared by dissolving the product in a proper amount of distilled water for injection.

What is claimed is:
1. α-(4-Oxo-4H-thiopyran-3-carboxamido)-p-hydroxybenzylpenicillin and its pharmaceutically acceptable acid addition salts.

* * * * *